US012723061B2

(12) United States Patent
Yim et al.

(10) Patent No.: US 12,723,061 B2

(45) Date of Patent: Sep. 1, 2026

(54) METHOD FOR PREVENTING OR TREATING CANCER BY BLOCKING EXCESSIVE PRODUCTION OF PHOSPHORYLATED VIMENTIN

(71) Applicant: INDUSTRY-UNIVERSITY COOPERATION FOUNDATION HANYANG UNIVERSITY ERICA CAMPUS, Gyeonggi-do (KR)

(72) Inventors: Hyungshin Yim, Seoul (KR); Hay Ran Jang, Gyeonggi-do (KR)

(73) Assignee: INDUSTRY-UNIVERSITY COOPERATION FOUNDATION HANYANG UNIVERSITY ERICA CAMPUS, Gyeonggi-do (KR)

( * ) Notice: Subject to any disclaimer, the term of this patent is extended or adjusted under 35 U.S.C. 154(b) by 475 days.

(21) Appl. No.: 18/034,415

(22) PCT Filed: Nov. 16, 2021

(86) PCT No.: PCT/KR2021/016817

§ 371 (c)(1),
(2) Date: Apr. 28, 2023

(87) PCT Pub. No.: WO2022/108309

PCT Pub. Date: May 27, 2022

(65) Prior Publication Data

US 2025/0263453 A1 Aug. 21, 2025

(30) Foreign Application Priority Data

Nov. 18, 2020 (KR) ........................ 10-2020-0154791
Nov. 30, 2020 (KR) ........................ 10-2020-0164854

(51) Int. Cl.

| | |
|---|---|
| ***A61P 35/04*** | (2006.01) |
| ***A61K 38/17*** | (2006.01) |
| ***A61K 48/00*** | (2006.01) |
| ***C07K 14/47*** | (2006.01) |
| ***C12N 15/113*** | (2010.01) |

(52) U.S. Cl.

CPC .......... *C07K 14/47* (2013.01); *A61K 38/1709* (2013.01); *A61K 48/005* (2013.01); *A61P 35/04* (2018.01); *C12N 15/113* (2013.01); *C12N 2310/531* (2013.01)

(58) Field of Classification Search

CPC .............................. A61P 35/04; C12N 15/113
See application file for complete search history.

(56) References Cited

U.S. PATENT DOCUMENTS 8,288,091 B2 * 10/2012 Bihain ..................... C12Q 1/68 435/6.12
8,999,921 B2 4/2015 Bang et al.
2012/0021974 A1 1/2012 Pall et al.
2019/0211088 A1 7/2019 Hall et al.

FOREIGN PATENT DOCUMENTS

EP 1559785 A1 * 8/2005 ............. G16B 30/00

OTHER PUBLICATIONS

Eckes, B. et al. Impaired wound healing in embryonic and adult mice lacking vimentin. Journal of Cell Science, 113, (2000), p. 2455-2462.

Kawa, K. et al. Inhibition of endocytic vesicle fusion by Plk1-mediated phosphorylation of vimentin during mitosis. Cell Cycle 13:1, p. 126-137; Jan. 1, 2014.

Khan, I. et al. Metastasis suppressors: functional pathways. Laboratory Investigation (2018) 98, p. 198-210.

Shibue, T. et al. Metastatic colonization: Settlement, adaptation and propagation of tumor cells in a foreign tissue environment. Seminars in Cancer Biology 21 (2011), p. 99-106.

Cai, X. P. et al. PLK1 promotes epithelial-mesenchymal transition and metastasis of gastric carcinoma cells. Am J Transl Res 2016;8(10): p. 4172-4183.

Wu, J. et al. Polo-like kinase 1 induces epithelial-to-mesenchymal transition and promotes epithelial cell motility by activating CRAF/ERK signaling. eLife Research article 2016; 5, 25 pages. DOI: 10.7554/eLife.10734.

Rizki, A. et al. Polo-like Kinase 1 Is Involved in Invasion through Extracellular Matrix. Cancer Res. Dec. 1, 2007; 67(23): p. 11106-11110. doi:10.1158/0008-5472.CAN-07-2348.

Ye, Z. et al. Prognostic Values of Vimentin Expression and Its Clinicopathological Significance in Non-Small Cell Lung Cancer: A Meta-Analysis of Observational Studies with 4118 Cases. PLOS ONE | DOI:10.1371/journal.pone.0163162 Sep. 22, 2016. 17 pages.

Eriksson, J.E. et al. Specific in vivo phosphorylation sites determine the assembly dynamics of vimentin Intermediate filaments. Journal of Cell Science 117, p. 919-932, doi:10.1242/jcs.00906.

Goldman, R.D. et al. The Function of Intermediate Filaments in Cell Shape and Cytoskeletal Integrity. The Journal of Cell Biology, vol. 134, No. 4, Aug. 1996, p. 971-983.

Valastyan, S. et al. Tumor Metastasis: Molecular Insights and Evolving Paradigms. Cell 147, Oct. 14, 2011, 18 pages. DOI 10.1016/j.cell.2011.09.024.

(Continued)

*Primary Examiner* — James D Schultz

*Assistant Examiner* — Keenan A Bates

(74) *Attorney, Agent, or Firm* — Casimir Jones, S.C.; Robert A. Goetz

(57) ABSTRACT

Finding that vimentin is overexpressed in cancer cells and the PLK1-induced phosphorylation of vimentin leads to tumorigenesis and cancer metastasis, the present invention suggests two methods of reducing frequency of interaction between PLK1 and vimentin as a strategy for preventing tumorigenesis and cancer metastasis by reducing the migration and infiltration of cancer, and provides an application thereof.

17 Claims, 41 Drawing Sheets

Specification includes a Sequence Listing.

(56) References Cited

OTHER PUBLICATIONS

Liu, C. et al. Vimentin contributes to epithelial-mesenchymal transition cancer cell mechanics by mediating cytoskeletal organization and focal adhesion maturation. Oncotarget, vol. 6, No. 18, 2015. p. 15966-15983.

International Search Report, Application No. PCT/KR2021/016817, dated Feb. 25, 2022, 3 pages.

Kim, T.W. et al. MicroRNA-17-5p regulates EMT by targeting vimentin in colorectal cancer. British Journal of Cancer. Jun. 17, 2020, vol. 123, pp. 1123-1130.

Havel, L.S. et al. Vimentin regulates lung cancer cell adhesion through a VAV2-Rac1 pathway to control focal adhesion kinase activity. Oncogene. Apr. 9, 2015;34(15):p. 1979-90 doi: 10.1038/onc.2014.123.

NCBI, GenBank Accession No. BAD96202.I. vimentin variant, pmtial [*Homo sapiens*]. Jul. 26, 2016.

* cited by examiner

SEQUENCE LISTING

```
<160> NUMBER OF SEQ ID NOS: 13

<210> SEQ ID NO 1
<211> LENGTH: 466
<212> TYPE: PRT
<213> ORGANISM: Homo sapiens
<220> FEATURE:
<221> NAME/KEY: VARIANT
<222> LOCATION: (327)
<223> OTHER INFORMATION: X is one of Gly, Ala, Val, Leu, Ile, Pro, Phe,
      Met, and Trp

<400> SEQUENCE: 1

Met Ser Thr Arg Ser Val Ser Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205
```

```
Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Xaa Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465


<210> SEQ ID NO 2
<211> LENGTH: 466
<212> TYPE: PRT
<213> ORGANISM: Homo sapiens
<220> FEATURE:
<221> NAME/KEY: VARIANT
<222> LOCATION: (339)
<223> OTHER INFORMATION: X is one of Gly, Ala, Val, Leu, Ile, Pro, Phe,
      Met, and Trp

<400> SEQUENCE: 2

Met Ser Thr Arg Ser Val Ser Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80
```

-continued

```
Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Xaa Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465
```

<210> SEQ ID NO 3
<211> LENGTH: 1401

-continued

<212> TYPE: DNA
<213> ORGANISM: Homo sapiens

<400> SEQUENCE: 3

```
atgtccacca ggtccgtgtc ctcgtcctcc taccgcagga tgttcggcgg cccgggcacc     60
gcgagccggc cgagctccag ccggagctac gtgactacgt ccacccgcac ctacagcctg    120
ggcagcgcgc tgcgccccag caccagccgc agcctctacg cctcgtcccc gggcggcgtg    180
tatgccacgc gctcctctgc cgtgcgcctg cggagcagcg tgcccggggt gcggctcctg    240
caggactcgg tggacttctc gctggccgac gccatcaaca ccgagttcaa gaacacccgc    300
accaacgaga aggtggagct gcaggagctg aatgaccgct tcgccaacta catcgacaag    360
gtgcgcttcc tggagcagca gaataagatc ctgctggccg agctcgagca gctcaagggc    420
caaggcaagt cgcgcctggg ggacctctac gaggaggaga tgcgggagct gcgccggcag    480
gtggaccagc taaccaacga caaagcccgc gtcgaggtgg agcgcgacaa cctggccgag    540
gacatcatgc gcctccggga gaaattgcag gaggagatgc ttcagagaga ggaagccgaa    600
aacaccctgc aatctttcag acaggatgtt gacaatgcgt ctctggcacg tcttgacctt    660
gaacgcaaag tggaatcttt gcaagaagag attgcctttt tgaagaaact ccacgaagag    720
gaaatccagg agctgcaggc tcagattcag gaacagcatg tccaaatcga tgtggatgtt    780
tccaagcctg acctcacggc tgccctgcgt gacgtacgtc agcaatatga aagtgtggct    840
gccaagaacc tgcaggaggc agaagaatgg tacaaatcca agtttgctga cctctctgag    900
gctgccaacc ggaacaatga cgccctgcgc caggcaaagc aggagtccac tgagtaccgg    960
agacaggtgc agtccctcgc ctgtgaagtg gatgccctta aaggaaccaa tgagtccctg   1020
gaacgccaga tgcgtgaaat ggaagagaac tttgccgttg aagctgctaa ctaccaagac   1080
actattggcc gcctgcagga tgagattcag aatatgaagg aggaaatggc tcgtcacctt   1140
cgtgaatacc aagacctgct caatgttaag atggcccttg acattgagat tgccacctac   1200
aggaagctgc tggaaggcga ggagagcagg atttctctgc ctcttccaaa cttttcctcc   1260
ctgaacctga gggaaactaa tctggattca ctccctctgg ttgataccca ctcaaaaagg   1320
acacttctga ttaagacggt tgaaactaga gatggacagg ttatcaacga aacttctcag   1380
catcacgatg accttgaata a                                              1401
```

<210> SEQ ID NO 4
<211> LENGTH: 1401
<212> TYPE: DNA
<213> ORGANISM: Homo sapiens

<400> SEQUENCE: 4

```
atgtccacca ggtccgtgtc ctcgtcctcc taccgcagga tgttcggcgg cccgggcacc     60
gcgagccggc cgagctccag ccggagctac gtgactacgt ccacccgcac ctacagcctg    120
ggcagcgcgc tgcgccccag caccagccgc agcctctacg cctcgtcccc gggcggcgtg    180
tatgccacgc gctcctctgc cgtgcgcctg cggagcagcg tgcccggggt gcggctcctg    240
caggactcgg tggacttctc gctggccgac gccatcaaca ccgagttcaa gaacacccgc    300
accaacgaga aggtggagct gcaggagctg aatgaccgct tcgccaacta catcgacaag    360
gtgcgcttcc tggagcagca gaataagatc ctgctggccg agctcgagca gctcaagggc    420
caaggcaagt cgcgcctggg ggacctctac gaggaggaga tgcgggagct gcgccggcag    480
gtggaccagc taaccaacga caaagcccgc gtcgaggtgg agcgcgacaa cctggccgag    540
```

-continued

```
gacatcatgc gcctccggga gaaattgcag gaggagatgc ttcagagaga ggaagccgaa    600

aacaccctgc aatctttcag acaggatgtt gacaatgcgt ctctggcacg tcttgacctt    660

gaacgcaaag tggaatcttt gcaagaagag attgcctttt tgaagaaact ccacgaagag    720

gaaatccagg agctgcaggc tcagattcag gaacagcatg tccaaatcga tgtggatgtt    780

tccaagcctg acctcacggc tgccctgcgt gacgtacgtc agcaatatga aagtgtggct    840

gccaagaacc tgcaggaggc agaagaatgg tacaaatcca agtttgctga cctctctgag    900

gctgccaacc ggaacaatga cgccctgcgc caggcaaagc aggagtccac tgagtaccgg    960

agacaggtgc agtccctcac ctgtgaagtg gatgccctta aaggaaccaa tgaggccctg   1020

gaacgccaga tgcgtgaaat ggaagagaac tttgccgttg aagctgctaa ctaccaagac   1080

actattggcc gcctgcagga tgagattcag aatatgaagg aggaaatggc tcgtcacctt   1140

cgtgaatacc aagacctgct caatgttaag atggcccttg acattgagat tgccacctac   1200

aggaagctgc tggaaggcga ggagagcagg atttctctgc ctcttccaaa cttttcctcc   1260

ctgaacctga gggaaactaa tctggattca ctccctctgg ttgataccca ctcaaaaagg   1320

acacttctga ttaagacggt tgaaactaga gatggacagg ttatcaacga aacttctcag   1380

catcacgatg accttgaata a                                             1401
```

<210> SEQ ID NO 5
<211> LENGTH: 58
<212> TYPE: DNA
<213> ORGANISM: Artificial Sequence
<220> FEATURE:
<223> OTHER INFORMATION: forword primer for target #1

<400> SEQUENCE: 5

```
ccgggtgaaa tggaagagaa ctttgctcga gcaaagttct cttccatttc actttttg       58
```

<210> SEQ ID NO 6
<211> LENGTH: 58
<212> TYPE: DNA
<213> ORGANISM: Artificial Sequence
<220> FEATURE:
<223> OTHER INFORMATION: reverse primer for target #1

<400> SEQUENCE: 6

```
aattcaaaaa gtgaaatgga agagaacttt gctcgagcaa agttctcttc catttcac       58
```

<210> SEQ ID NO 7
<211> LENGTH: 58
<212> TYPE: DNA
<213> ORGANISM: Artificial Sequence
<220> FEATURE:
<223> OTHER INFORMATION: forword primer for target #2

<400> SEQUENCE: 7

```
ccgggcagaa gaatggtaca aatccctcga gttatttgta ccattcttct gctttttg       58
```

<210> SEQ ID NO 8
<211> LENGTH: 58
<212> TYPE: DNA
<213> ORGANISM: Artificial Sequence
<220> FEATURE:
<223> OTHER INFORMATION: reverse primer for target #2

<400> SEQUENCE: 8

```
aattcaaaaa gcagaagaat ggtacaaatc cctcgagtta tttgtaccat tcttctgc       58
```

-continued

```
<210> SEQ ID NO 9
<211> LENGTH: 58
<212> TYPE: DNA
<213> ORGANISM: Artificial Sequence
<220> FEATURE:
<223> OTHER INFORMATION: forword primer for target #3

<400> SEQUENCE: 9

ccggtgaaga aactccacga agaggctcga gcctcttcgt ggagtttctt catttttg       58


<210> SEQ ID NO 10
<211> LENGTH: 58
<212> TYPE: DNA
<213> ORGANISM: Artificial Sequence
<220> FEATURE:
<223> OTHER INFORMATION: reverse primer for target #3

<400> SEQUENCE: 10

aattcaaaaa tgaagaaact ccacgaagag gctcgagcct cttcgtggag tttcttca       58


<210> SEQ ID NO 11
<211> LENGTH: 21
<212> TYPE: DNA
<213> ORGANISM: Artificial Sequence
<220> FEATURE:
<223> OTHER INFORMATION: shRNA #1

<400> SEQUENCE: 11

gtgaaatgga agagaacttt g                                               21


<210> SEQ ID NO 12
<211> LENGTH: 21
<212> TYPE: DNA
<213> ORGANISM: Artificial Sequence
<220> FEATURE:
<223> OTHER INFORMATION: shRNA #2

<400> SEQUENCE: 12

gcagaagaat ggtacaaatc c                                               21


<210> SEQ ID NO 13
<211> LENGTH: 21
<212> TYPE: DNA
<213> ORGANISM: Artificial Sequence
<220> FEATURE:
<223> OTHER INFORMATION: shRNA #3

<400> SEQUENCE: 13

tgaagaaact ccacgaagag g                                               21
```

METHOD FOR PREVENTING OR TREATING CANCER BY BLOCKING EXCESSIVE PRODUCTION OF PHOSPHORYLATED VIMENTIN

SEQUENCE LISTING

The text of the computer readable sequence listing filed Jun. 5, 2024, titled "MUHA_41849_251_SequenceListing_Corrected.txt" created Jun. 5, 2024, having a file size of 13,910 bytes, is hereby incorporated by reference in its entirety.

TECHNICAL FIELD

The present disclosure proposes two types of methods for reducing the frequency of interaction between PLK1 and vimentin as a strategy for preventing tumorigenesis and cancer metastasis by reducing the migration and invasion of cancer and provides an application thereof, by confirming that vimentin is overexpressed in cancer cells and the PLK1-induced phosphorylation of vimentin leads to tumorigenesis and cancer metastasis.

First, the present disclosure provides a method for reducing the interaction between wild-type vimentin and PLK1 by providing a vimentin mutant in which a region phosphorylated by PLK1 is mutated while maintaining binding force with PLK1.

Second, the present disclosure provides a method for suppressing the production of excessively phosphorylated vimentin ultimately by suppressing the expression of vimentin, which is excessively expressed in cancer cells, using shRNA targeting vimentin.

BACKGROUND ART

Vimentin is an intermediate filament protein mainly expressed in mesenchymal cells and serves to maintain cell homeostasis by forming a cytoskeletal network with microtubules and microfilaments (Goldman, R. D. et al., J Cell Biol 134 (1996) 971-983). In particular, in an epithelial-mesenchymal transition (EMT) process, the vimentin is known to be an important regulator that regulates the migration and invasion of cells (Eckes, B. et al., J Cell Sci 111 (Pt 13) (1998) 1897-1907; Liu, C. Y. et al., Oncotarget 6 (2015) 15966-15983). It has been reported that such vimentin is overexpressed in breast cancer, lung cancer, gastric cancer and many other solid cancers, and the expression of vimentin increases as a malignant stage of cancer increases (Yamashita, N. et al., J Cancer Res Clin Oncol 139 (2013) 739-746; Ye, Z. et al., PLOS One 11 (2016) e0163162; Yin, S. et al., Pathol Res Pract 214 (2018) 1376-1380). In solid cancers, the vimentin is involved in cytoskeletal reconstruction during the EMT, which is known to promote the migration and invasion of cancer cells by regulating signaling related to the EMT. In addition, embryonic cells lacking vimentin have reduced cell migration, and in the case of vimentin-deficient mice, it has been reported that the healing of a wound region is poor due to impaired migration of myofibroblasts at the wound region (Eckes, B. et al., J Cell Sci 111 (Pt 13) (1998) 1897-1907; Eckes, B. et al., J Cell Sci 113 (Pt 13) (2000) 2455-2462). It is known that the phosphorylation of vimentin is involved in cell migration, and it is known that when vimentin is phosphorylated, the phosphorylated vimentin increases the cell migration by regulating the binding structure of intermediate filaments (IF) (Eriksson, J. E. et al., J Cell Sci 117 (2004) 919-932; Zhu, Q. S. et al., Oncogene 30 (2001) 457-470). Although such vimentin is known as a marker for the EMT, its role in mediating this process is not precisely known.

Polo-like phosphatase 1 (PLK1) has recently been studied as a target molecule that causes carcinogenesis and metastasis, and based on this, research on the development of anticancer drugs through the development of inhibitors for PLK1 has been conducted competitively on multinational companies (Yim, Anti-Cancer Drugs 24 (2013) 999-1006; Yim and Erikson, Mutation Research Reviews Mutation Research, 761 (2014) 31-39). PLK1 structurally has an enzymatic domain with phosphatase activity and a polobox domain that binds to a substrate, and phosphorylation at position T210 induces activation of PLK1. The phosphatase of PLK1 activated by the binding of the substrate to the polobox domain is an enzyme that induces phosphorylation on Ser/Thr residues of the substrate (Barr et al., Nat Rev Mol Cell Biol 5 (2004) 429-440). Functionally, its expression is increased in growing and dividing cells, but in particular, the expression and activity of the phosphatase peak during a cell division phase of a cell cycle. Accordingly, it is known that its expression rate is also high in rapidly growing cancer cells (Yim, Anti-Cancer Drugs 24 (2013) 999-1006; Yim and Erikson, Mutation Research Reviews Mutation Research, 761 (2014) 31-39), and it has been experimentally reported that the expression thereof is increased in many cases during a graded malignant alteration of cancer cells. In particular, it has been reported that the expression thereof increases as the malignant stage increases in non-small cell lung cancer, head and neck cancer, laryngeal cancer, breast cancer, liver cancer, endometrial cancer, colon cancer, ovarian cancer, pancreatic cancer, and prostate cancer (Yim, Anti-Cancer Drugs 24 (2013) 999-1006; Yim and Erikson, Mutation Research Reviews Mutation Research, 761 (2014) 31-39). According to recent research reports and studies by the present inventors, it has been observed that active-type PLK1 is involved in increasing cancer metastasis, and accordingly, the value of PLK1 as a molecular target for the treatment of metastatic cancer has recently begun to emerge (Cai et al., Am J Transl Res 8 (2016) 4172-4183; Wu et al., eLife 5 (2016) e10734; individual research results). Therefore, anticancer drugs targeting the functional regulation of the phosphorylated substrate of PLK1 are expected to be effective in the treatment of not only primary cancer but also metastatic cancer.

The cancer metastasis is a phenomenon that appears as a result of cancer progression, but even if primary cancer is substantially removed or treated, if metastasis may not be prevented, the survival rate is very low due to cancer recurrence or the like. Metastatic cancer accounts for 90% of death in all cancer patients, and thus, the risk thereof may be estimated (Valastyan, S. and Weinberg, R. A., Cell 147 (2011) 275-292; Khan, I. and Steeg, P. S., Lab Invest 98 (2018) 198-210). It is considered that the larger the size of cancer, the higher the rate of metastasis to peripheral lymph nodes and other tissues, but although the size of cancer is small, there is a case where the metastasis occurs, so that a relationship between cancer metastasis and proliferation has not yet been clearly identified (Valastyan, S. and Weinberg, R. A., Cell 147 (2011) 275-292; Shibue, T. and Weinberg, Semin Cancer Biol 21 (2011) 99-106). In the treatment of cancer, inhibition of cancer cell proliferation and inhibition of metastasis are not always the same effect, and in terms of the fact that the treatment efficiency of many cancers may be dramatically improved if cancer metastasis may be inhibited, it is necessary to develop a therapeutic target or therapeutic agent that effectively inhibits cancer metastasis and invasion for the treatment of metastatic cancer.

DISCLOSURE OF THE INVENTION

Technical Goals

The present disclosure relates to a cancer cell killing effect of a point-mutated vimentin protein and to a use of inhibitors for migration and invasion of metastatic cancer cells. The present disclosure also relates to a use as an apoptosis inducer using an action that sensitively induces apoptosis in metastatic cancer cells as well as general solid cancers. The present disclosure may be usefully used to treat various solid cancers and metastatic cancers.

Thus, the present disclosure has been made in an effort to provide a vimentin mutant in which amino acid at position 327 or 339 is substituted and a vector expressing the vimentin mutant.

In addition, the present disclosure has also been made in an effort to provide a pharmaceutical composition for preventing or treating cancer including the mutant or vector as an active ingredient.

In addition, the present disclosure has also been made in an effort to provide a shRNA effective for inhibiting the expression of a vimentin protein for use in the prevention or treatment of cancer.

However, technical goals to be achieved are not limited to those described above, and other goals not mentioned above are clearly understood by one of ordinary skill in the art from the following description.

Technical Solutions

In order to achieve the aspect of the present disclosure, the present disclosure provides a vimentin non-phosphorylated point mutant including or consisting of an amino acid sequence of SEQ ID NO: 1 or SEQ ID NO: 2.

As an embodiment of the present disclosure, the vimentin non-phosphorylated point mutant may be a vimentin protein (SEQ ID NO: 1) in which amino acid at position 327, threonine is substituted with glycine (Gly), alanine (Ala), valine (Val), leucine (Leu), isoleucine (Ile), proline (Pro), phenylalanine (Phe), methionine (Met) or tryptophan (Trp), desirably alanine.

As another embodiment of the present disclosure, the vimentin non-phosphorylated point mutant may be a vimentin protein (SEQ ID NO: 2) in which amino acid at position 339, serine is substituted with glycine, alanine, valine, leucine, isoleucine, proline, phenylalanine, methionine or tryptophan, desirably alanine.

In addition, the present disclosure provides a recombinant vector including a gene encoding the vimentin mutant.

As an embodiment of the present disclosure, the gene encoding the vimentin mutant may include or consist of a nucleotide sequence of SEQ ID NO: 3 or SEQ ID NO: 4.

As another embodiment of the present disclosure, the recombinant vector may be a viral vector, desirably a lentiviral vector.

In addition, the present disclosure provides a pharmaceutical composition for the prevention or treatment of cancer including the vimentin mutant or the recombinant vector.

In addition, the present disclosure provides a pharmaceutical composition for inhibiting cancer metastasis including the vimentin mutant or the recombinant vector.

As an embodiment of the present disclosure, the composition may inhibit cancer metastasis by reducing the migration and invasion of cancer cells.

In addition, the present disclosure provides a method for the prevention or treatment of cancer including administering the vimentin mutant or the recombinant vector to a subject.

In addition, the present disclosure provides a use of the vimentin mutant or the recombinant vector for preparing a drug for preventing or treating cancer.

In addition, the present disclosure provides shRNA (short hairpin RNA) for inhibiting the vimentin expression.

The shRNA for inhibiting the vimentin expression of the present disclosure may include or consist of any one of nucleotide sequences of SEQ ID NOs: 11 to 13, but may desirably include or consist of a nucleotide sequence of SEQ ID NO: 11.

In addition, the present disclosure provides a pharmaceutical composition for the prevention or treatment of cancer including the shRNA as an active ingredient.

As one embodiment of the present disclosure, the composition may inhibit tumorigenicity.

As another embodiment of the present disclosure, the composition may inhibit cancer metastasis by reducing the migration and invasion of cancer cells. That is, the composition of the present disclosure may be provided for use for the prevention of metastatic cancer.

As yet another embodiment of the present disclosure, the composition may further include a vimentin mutant including or consisting of the amino acid sequence of SEQ ID NO: 1 or SEQ ID NO: 2.

In addition, the present disclosure provides a pharmaceutical composition for inhibiting cancer metastasis including the shRNA.

In addition, the present disclosure provides a method for preventing or treating cancer including administering the shRNA to a subject.

In addition, the present disclosure provides a use of the shRNA for the preparation of a drug for preventing or treating cancer.

Meanwhile, in the present disclosure, the cancer may be a solid cancer, the solid cancer may be a non-small cell lung cancer, and the non-small cell lung cancer may be particularly adenocarcinoma.

In addition, in the present disclosure, the subject may be a human in need of cancer prevention or treatment, and may be a patient who has already developed cancer and being treated, or a patient for preventing metastasis after complete cure of cancer.

Effects

According to the present disclosure, the vimentin mutant binds to PLK1 overexpressed competitively with wild-type vimentin in cancer cells while maintaining its binding ability with PLK1 to inhibit tumorigenesis and cancer metastasis. In addition, the vector expressing the mutant in cancer cells may be provided to suppress the migration and invasion of cancer and inhibit tumorigenesis. The non-phosphorylated point mutants of the present disclosure are safe because they do not affect the intrinsic function of vimentin in normal cells, and may be usefully used to treat various diseases caused by abnormal cell growth, especially degenerative diseases such as primary and metastatic solid cancers and leukemia.

In addition, the vimentin shRNA and/or vimentin mutants of the present disclosure have a strong inhibitory effect on metastasis, invasion and selective tumorigenesis of cancer cells, and thus, it is expected to be useful in the treatment of various diseases caused by abnormal cell growth, especially degenerative diseases such as primary and metastatic solid cancers and leukemia.

BRIEF DESCRIPTION OF DRAWINGS

FIG. 1A: a graph analyzing a related pathway of invasion cells in which active PLK1 is expressed in cancer metastasis conditions of lung cancer cells A549 through KEGG 2019 pathway analysis.

FIG. 1B: a schematic diagram showing association between genes expressed in invasion cells in which active PLK1 is expressed under cancer metastasis conditions of lung cancer cell A549 and ECM-related genes through GeneMANIA database analysis.

FIG. 1C: a graph of analyzing the survival rate of lung cancer patients of different species according to the expression of PLK1 and vimentin through KM PLOTTER analysis.

FIG. 1D: a graph of analyzing the survival rate of lung cancer patients depending on a stage of lung cancer progression according to the expression of PLK1 and vimentin through KM PLOTTER analysis.

FIG. 1E: a graph showing the expression of epithelial-mesenchymal transition markers in various types of lung cancer cells treated with TGF-β to induce cancer metastasis through heatmap analysis.

FIG. 1F: a graph showing the mRNA expression of vimentin, active PLK1, and epithelial-mesenchymal transition markers in lung cancer cells A549 and NCI-H460 treated with TGF-β using real-time PCR.

FIG. 1G: a result of observing the protein expression of vimentin, active PLK1, and epithelial-mesenchymal transition markers in lung cancer cells A549 and NCI-H460 treated with TGF-β by an immunoblot method.

FIG. 1H: a graph showing a protein expression of G vimentin and active PLK1.

FIG. 2A: a result of observing an interaction between vimentin and PLK1 by immunoprecipitation using a PLK1 antibody under conditions for treating A549 cells with 2.5 ng/ml TGF-β.

FIG. 2B: a result of observing an interaction between vimentin and PLK1 by immunoprecipitation using a PLK1 antibody under conditions for treating NCI-H460 cells with 2.5 ng/ml TGF-β.

FIG. 2C: a result of observing active PLK1 phosphorylated vimentin by performing a phosphorylation enzyme reaction method with active PLK1 (PLK1 TD) using GST-labeled vimentin.

FIG. 2D: a result of confirming a candidate site capable of phosphorylating vimentin phosphorylated by PLK1 through liquid chromatography mass spectrometry.

FIG. 2E: a result of performing a phosphorylation enzyme reaction method using a non-phosphorylated point mutant protein in which a candidate site for phosphorylation of vimentin is substituted with alanine using a site-specific mutation substitution method and an active PLK1.

FIG. 2F: a result of observing a reduction of phosphorylation of vimentin and PLK1 by phosphatase (CIP) treatment after A549 cells are treated with 2.5 ng/ml TGF-β.

FIG. 2G: a result of observing a reduction of phosphorylation of vimentin and PLK1 by phosphatase (CIP) treatment after NCI-H460 cells are treated with 2.5 ng/ml TGF-β.

FIG. 3A: a result of observing the overexpression of a vimentin protein and a change in mesenchymal transition marker (N-cadherin) through immunoblot after expressing vimentin phosphorylated and non-phosphorylated point mutants in lung cancer cells NCI-H460.

FIG. 3B: a result of observing the overexpression of a vimentin mRNA and an mRNA change in mesenchymal transition marker (N-cadherin) through real-time PCR after expressing vimentin phosphorylated and non-phosphorylated point mutants in lung cancer cells NCI-H460.

FIG. 3C: a result of observing the degree of cell proliferation of cells expressing each point mutant over time after expressing vimentin phosphorylated and non-phosphorylated point mutants in lung cancer cells NCI-H460.

FIG. 3D: a result of observing the migration pattern of cells with a microscope through a migration assay using an insert in lung cancer cells NCI-H460 expressing vimentin phosphorylated and non-phosphorylated point mutants.

FIG. 3E: a graph showing the migration pattern of cancer cells using an Odyssey infrared imaging system analysis device with respect to the intensity of cancer cells stained with crystal violet moving through an insert in a migration assay using an insert.

FIG. 3F: a result of observing the invasion pattern of cells through an invasion assay using a matrigel and an insert in lung cancer cells NCI-H460 expressing vimentin phosphorylated and non-phosphorylated point mutants.

FIG. 4A: a result of observing metastatic cancer formation and inhibitory effects in lungs of mice when lung cancer cells expressing vimentin phosphorylated and non-phosphorylated point mutants are intravenously injected.

FIG. 4B: a graph showing metastatic cancer formation and inhibitory effects in mice by intravenous injection of lung cancer cells expressing vimentin phosphorylated and non-phosphorylated point mutants with frequency values of metastatic cancer formation in each experimental group.

FIG. 4C: a graph showing the survival rate of each experimental group when lung cancer cells expressing vimentin phosphorylated and non-phosphorylated point mutants are intravenously injected.

FIG. 4D: a result of observing cancer formation and inhibitory effects in each experimental group by H&E staining and Ki-67 staining of cancer tissue metastasized to the lungs of mice and produced when lung cancer cells expressing vimentin phosphorylated and non-phosphorylated point mutants are intravenously injected.

FIG. 4E: a result showing quantifying and graphing cancer formation and inhibitory effects in each experimental group by H&E staining of cancer tissue metastasized to the lungs of mice and produced.

FIG. 4F: a result showing quantifying and graphing cancer formation and inhibitory effects in each experimental group by Ki-67 staining of cancer tissue metastasized to the lungs of mice and produced.

FIG. 4G: a result of observing changes in epithelial-mesenchymal transition protein markers and immune evasion factor proteins by crushing lung tissues obtained from mice when lung cancer cells expressing vimentin phosphorylated and non-phosphorylated point mutants are intravenously injected.

FIG. 4H: a graph showing quantifying a change in the expression of PD-L1, an immune evasion factor protein for each experimental group by crushing lung tissues obtained from mice when lung cancer cells expressing vimentin phosphorylated and non-phosphorylated point mutants are intravenously injected.

FIG. 5A: a result showing the inhibition degree of vimentin expression by each vimentin shRNA treatment in lung cancer cell NCI-H460 as a protein expression pattern.

FIG. 5B: a graph showing the inhibition degree of vimentin expression by each vimentin shRNA treatment in lung cancer cell NCI-H460 as an mRNA expression pattern.

FIG. 6A: a result showing protein expression patterns of epithelial-mesenchymal transition markers N-cadherin and E-cadherin and an immune evasion factor PD-L1 in a cancer cell metastasis environment in which the inhibition of vimentin expression is induced by TGF-β treatment by vimentin shRNA treatment in lung cancer cells NCI-H460.

FIG. 6B: a graph showing mRNA expression patterns of epithelial-mesenchymal transition markers N-cadherin and E-cadherin and an immune evasion factor PD-L1 in a cancer cell metastasis environment in which the inhibition of vimentin expression is induced by TGF-β treatment by vimentin shRNA treatment in lung cancer cells NCI-H460.

FIG. 6C: a result showing protein expression patterns of epithelial-mesenchymal transition markers N-cadherin and E-cadherin and an immune evasion factor PD-L1 in a cancer cell metastasis environment in which the inhibition of vimentin expression is induced by TGF-β treatment by vimentin shRNA treatment in lung cancer cells A549.

FIG. 6D: a graph showing mRNA expression patterns of epithelial-mesenchymal transition markers N-cadherin and E-cadherin and an immune evasion factor PD-L1 in a cancer cell metastasis environment in which the inhibition of vimentin expression is induced by TGF-β treatment by vimentin shRNA treatment in lung cancer cells A549.

FIG. 6E: a graph of converting the migration of cancer cells by vimentin shRNA treatment into a relative percentage, when a relative distance of cells after 72 hours is 0% in a control group in a cancer cell metastasis environment in which the inhibition of vimentin expression is induced by TGF-β treatment by vimentin shRNA treatment in lung cancer cells NCI-H460.

FIG. 6F: a result showing patterns of reducing the invasion of cancer cells in which the inhibition of vimentin expression is induced by TGF-β treatment by vimentin shRNA treatment in lung cancer cells NCI-H460.

FIG. 6G: a result showing patterns of inhibiting the tumorigenesis of cancer cells in which the inhibition of vimentin expression is induced by TGF-β treatment by vimentin shRNA treatment in lung cancer cells NCI-H460.

FIG. 6H: a result of observing through immunoblotting overexpressing a wild type (WT), and phosphorylated (S339E) and non-phosphorylated (S339A) point mutants of vimentin again after inhibiting the vimentin expression by vimentin shRNA treatment in lung cancer cells NCI-H460.

FIG. 6I: a result of observing an effect on the migration of cancer cells by overexpression of a wild type (WT), and phosphorylated (S339E) and non-phosphorylated (S339A) point mutants of vimentin again under conditions for inhibiting the vimentin expression by vimentin shRNA treatment in lung cancer cells NCI-H460.

FIG. 6J: a result of observing an effect on the invasion of cancer cells by overexpression of a wild type (WT), and phosphorylated (S339E) and non-phosphorylated (S339A) point mutants of vimentin again under conditions for inhibiting the vimentin expression by vimentin shRNA treatment in lung cancer cells NCI-H460.

BEST MODE FOR CARRYING OUT THE INVENTION

Figure 1A:
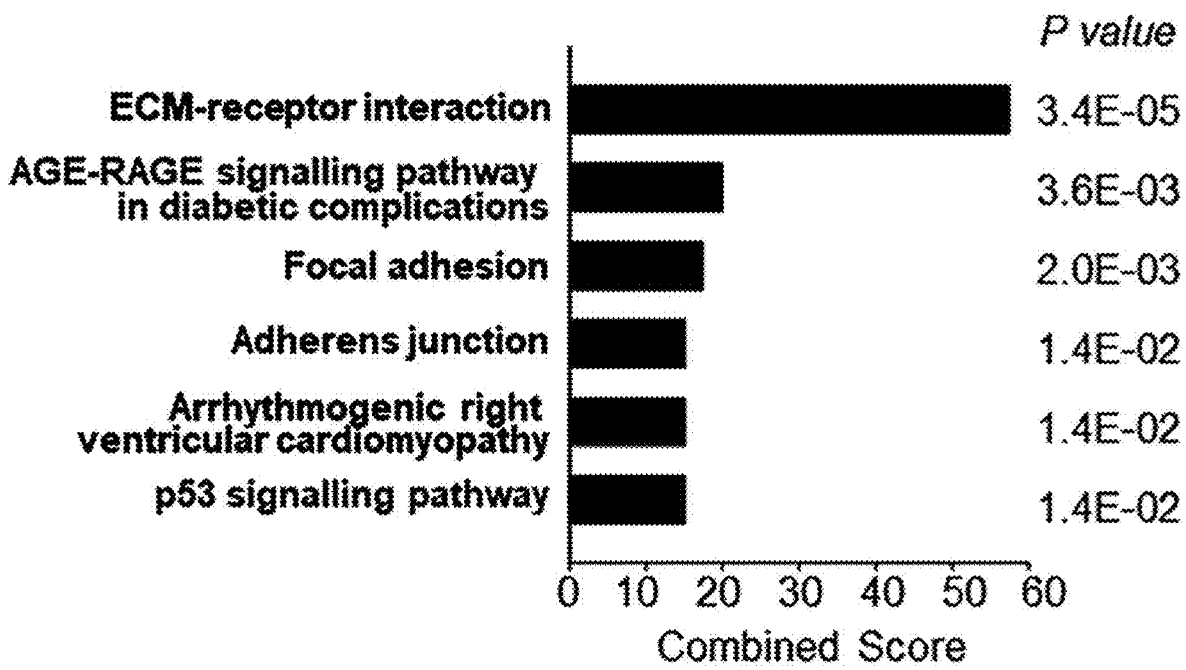
FIGS. 1A to 1H are results of analyzing clinical association between vimentin and active PLK1 in metastatic lung cancer cells.

The present inventors confirmed that phosphorylation of vimentin by PLK1 contributed to cancer metastasis while studying polo-like kinase 1 (PLK1), confirmed that migration and invasion of cancer were significantly reduced as a result of searching for the phosphorylation site of vimentin by PLK1 to induce mutations, confirmed that the migration and invasion of cancer were significantly reduced when the expression of vimentin was knocked down, and then completed the present disclosure.

PLK1 is known to be overexpressed in cancer cells as a proto-oncogene, and studies on the PLK1 molecule as a target for cancer treatment have been actively conducted. However, PLK1 is a phosphatase involved in various signaling systems such as a cell cycle, and the inhibition of PLK1 has a problem that it is difficult to exclude a possibility of other actions other than an effect of suppressing tumor growth, etc., and an original function of PLK1 is not smoothly performed in the action in normal cells.

PLK1 has been reported to be phosphorylated at serine(S) sites at positions 83 and 459 of vimentin (Eriksson, J. E. et al., Cancer Res 67 (2007) 11106-11110; Keisuke Ikawa et al., Cell cycle 13 (2014) 126-137), and no studies have been reported on whether point mutants in these sites block metastasis, invasion, or tumorigenesis of cancer cells.

Through specific experiments, the present inventors confirmed that the expression of active PLK1 and vimentin increased as the progression stage of cancer was higher in cancer cells, especially non-small cell lung cancer, that is, as the cancer progressed to metastatic cancer, and predicted that vimentin was a factor included in a cancer metastasis promoting signaling system of PLK1 (Example 1).

The present inventors intended to target sub-molecules in a mechanism by which PLK1 is involved in cancer proliferation and metastasis, specifically observed increased binding of PLK1 and vimentin by performing immunoprecipitation after inducing metastatic lung cancer with TGF-β in order to confirm the interaction between PLK1 and vimentin (Example 2).

Meanwhile, vimentin was a filament protein that served to maintain cell homeostasis by forming a cytoskeleton network, and the present inventors tried to devise a method capable of blocking only an action in the stage of cancer metastasis while maintaining the original function of vimentin in normal cells. The present inventors confirmed that as progressing to non-small cell lung cancer, especially metastatic cancer, PLK1 and vimentin were overexpressed, and PLK1 bound to vimentin to induce phosphorylation of vimentin. In other words, assuming that phosphorylation of vimentin by PLK1 was a required condition for cancer metastasis, only the phosphorylation of vimentin by PLK1 was prevented to inhibit cancer metastasis. Therefore, the present inventors searched for the phosphorylation sites of vimentin by PLK1 and selected Thr-327, Thr-336, and Ser-339 as candidate phosphorylation sites. Subsequently, mutants in which amino acids were substituted at the positions were constructed, and a phosphatase reaction method was performed to specify Thr-327 and Ser-339 as phosphorylation sites by PLK1 (Example 2).

Next, the present inventors constructed lentivirus expressing a mutant in which serine or threonine at position 327 or 339 was substituted with alanine and a mutant in which serine at position 83 or 459 was substituted with alanine, which was reported as a phosphorylation site by PLK1 in addition to the position, and confirmed the migration, invasion, and tumorigenesis of cancer cells by transforming cancer cells using the lentivirus. As a result, it was confirmed that cancer cells transfected a mutation in which amino acid at position 327 or 339 was substituted with alanine showed particularly low migration, invasion, and tumorigenesis, and thus, it could be seen that amino acids at positions 327 and 339 of vimentin were effective as a target for blocking phosphorylation by PLK1 (Examples 3 to 7).

Figure 3A:
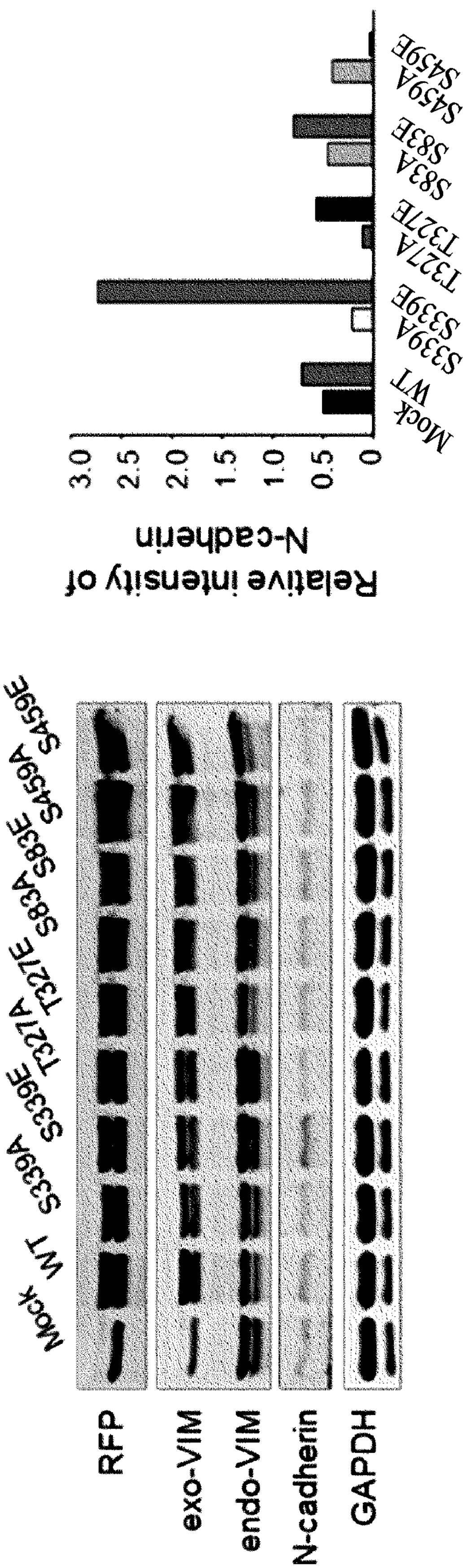
FIGS. 3A to 3F are experiments of measuring an effect of overexpression of phosphorylated and non-phosphorylated mutants of vimentin on the migration and invasion of cancer cells in lung cancer cells NCI-H460.
Figure 3B:
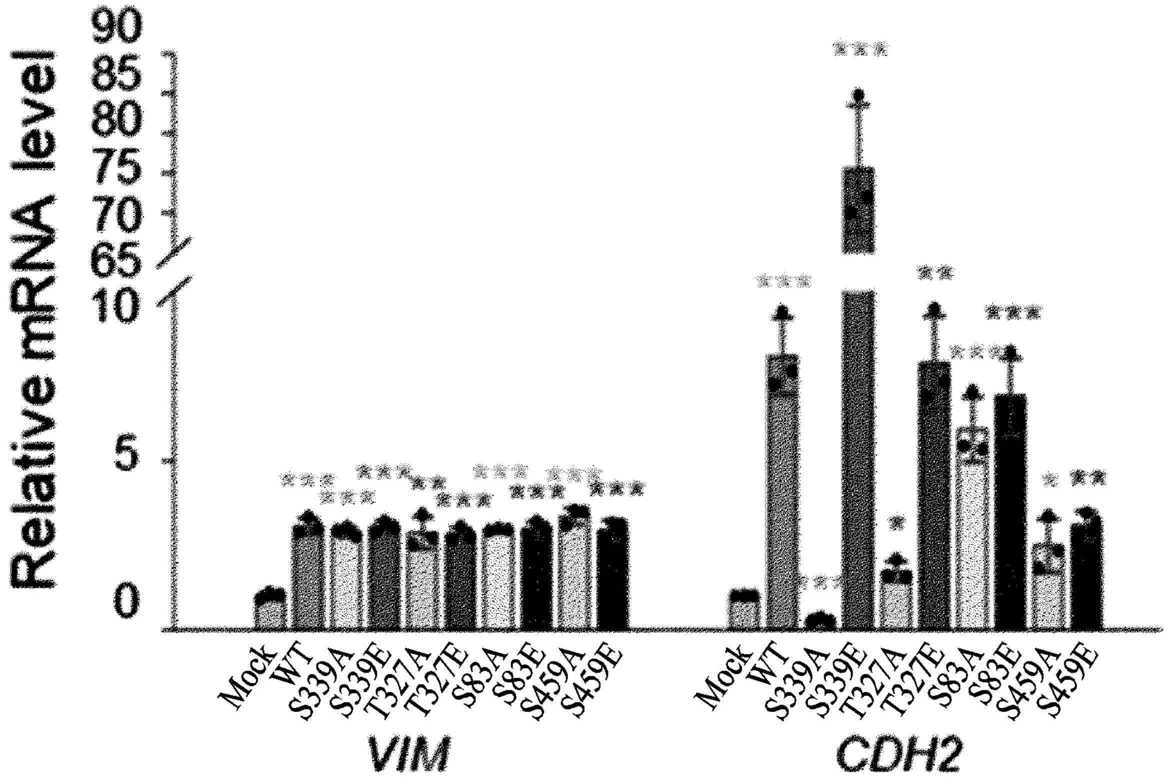
Figure 3C:
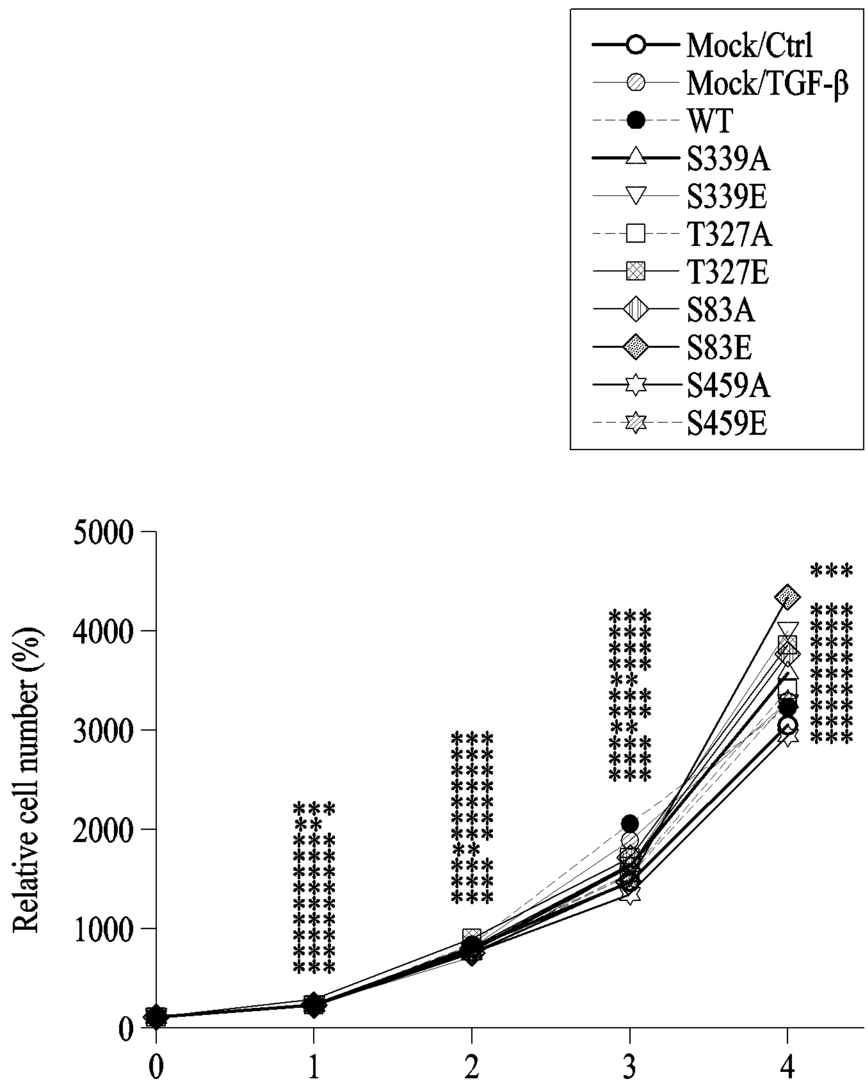
Figure 3D:
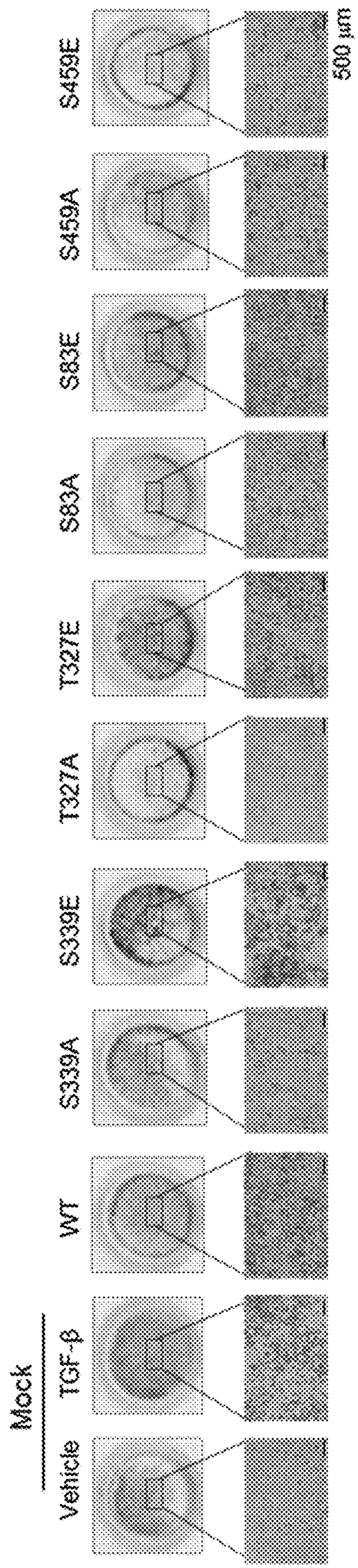
Figure 3E:
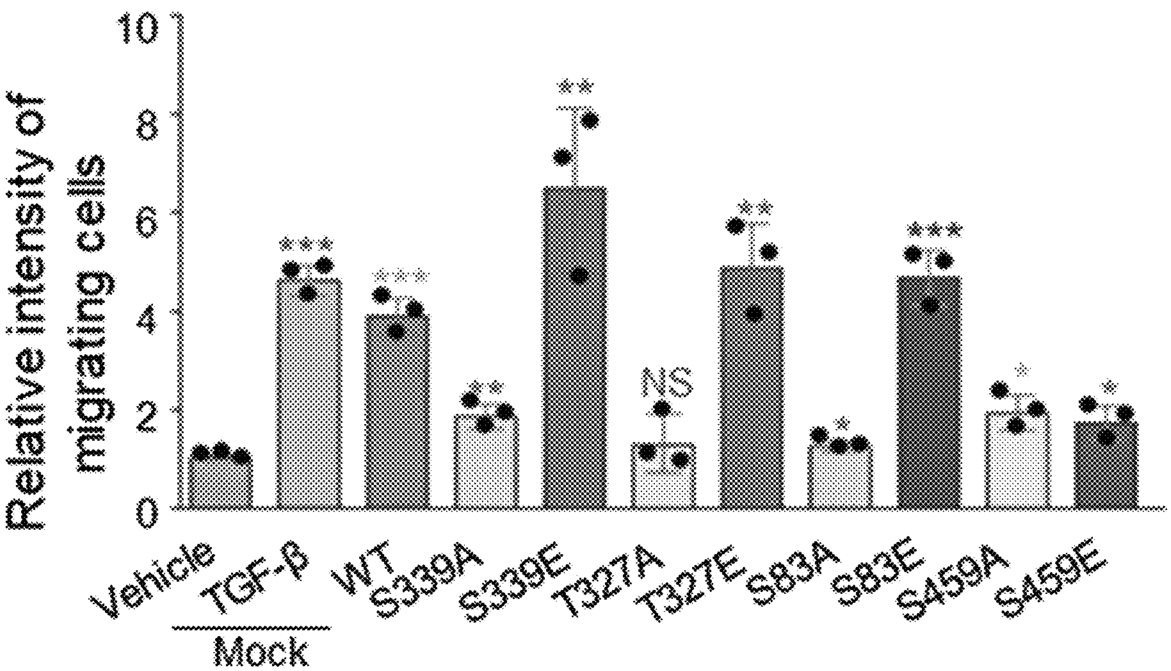

More specifically, the present inventors conducted a migration assay of cancer cells to observe the metastasis of cancer cells in NCI-H460 cells expressing each protein of phosphorylated and non-phosphorylated point mutants of vimentin through specific experiments (FIGS. 3D to 3E). As a result of the study, in an experimental group in which the phosphorylated point mutants S339E, T327E, and S83E of vimentin were expressed, it was observed that the migration of cancer cells increased more than a positive control group treated with TGF-β (2.5 ng/ml). Contrary to this, the migration of cancer cells expressing non-phosphorylated point mutants (S339A, T327A, and S83A) proteins was reduced (Example 5).

Figure 3F:
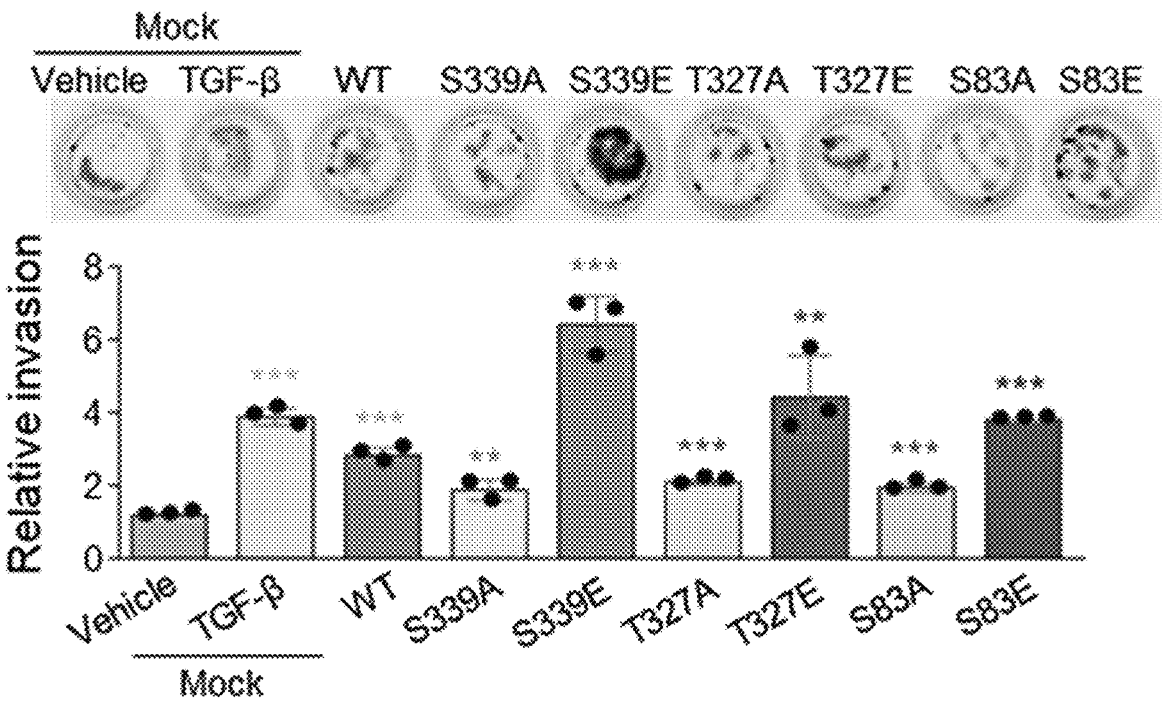

In addition, the present inventors conducted experiments on the promotion and inhibition of invasion in cancer cells using a phosphorylated point mutant and a non-phosphorylated point mutant of vimentin through specific experiments. The invasion of cancer cells was observed using an invasion assay using Matrigel (FIG. 3F). First, in order to evaluate the invasion, cells expressing each vimentin point mutant were dispensed in matrigel inserts with a serum-free medium, and serum-containing medium was dispensed on an experimental plate and cultured for 5 days. The invaded cancer cells are observed by staining with crystal violet, dissolved in DMSO, and absorbance was measured at a wavelength of 590 nm. As a result of the study, it was observed that a lung cancer cell group expressing the phosphorylated point mutant protein of vimentin had an increased invasion compared to a control group and a wild type of vimentin. In particular, the highest invasion of cancer cells was observed in a S339 phosphorylated point mutant of vimentin. On the other hand, it was observed that the invasion was reduced in the lung cancer cell group expressing a non-phosphorylated point mutant protein of vimentin. Therefore, it was possible to observe an effect of promoting the invasion of cancer cells by the phosphorylated point mutant of vimentin and an effect of inhibiting the invasion of cancer cells by the non-phosphorylated point mutant of vimentin in lung cancer cells (Example 6).

In addition, in the present disclosure, in order to examine the involvement with cancer metastasis and tumorigenesis of proteins expressing PLK1-induced phosphorylated and non-phosphorylated point mutants of vimentin in an animal model through specific experiments, BALB/c nude mice were tail-intravenously injected with NCI-H460 cells overexpressing each vimentin mutant protein, raised for 8 weeks and opened, and then metastasis and tumorigenesis of cancer cells were observed in organs (FIG. 4). In the lungs in an animal group injected with cells expressing the phosphorylated point mutant of vimentin, cancer metastasis and tumorigenesis were observed more frequently than cells expressing a control, a wild type, and a non-phosphorylated point mutant. On the other hand, it was confirmed that the lungs in the animal group injected with cells expressing non-phosphorylated point mutants of vimentin had low tumorigenesis. Accordingly, it was possible to observe the effect of promoting the tumorigenesis of cancer cells by the phosphorylated point mutant protein at a novel phosphorylation site by PLK1 of vimentin, and an effect of inhibiting the tumorigenicity of cancer cells by the non-phosphorylated point mutant protein of vimentin was observed (Example 7).

Therefore, the present disclosure may provide, as a target, amino acids at positions 327 and 339 of vimentin as phosphorylation blocking sites of vimentin by PLK1. In addition, the present disclosure may provide a vimentin mutant in which S339 and/or T327 amino acids are substituted for use in the prevention and treatment of cancer.

Meanwhile, PLK1 structurally includes an enzyme activity domain with phosphatase activity and a polobox domain that binds to a substrate, and a vimentin mutant, in which an amino acid is substituted at position 327 or 339, maintains binding force with PLK1 as it is. Accordingly, the mutant in which the amino acid (amino acid at position 327 or 339) in the phosphorylation site is substituted competitively binds to PLK1 with wild-type vimentin, and as a result, phosphorylation of wild-type vimentin may decrease in a concentration-dependent manner of the mutant.

In the vimentin mutant of the present disclosure, S339 and/or T327 in the wild-type vimentin protein is substituted with glycine, alanine, valine, leucine, isoleucine, proline, phenylalanine, methionine or tryptophan, and through a specific experiment, the effect thereof was confirmed using a mutant substituted with alanine.

Next, the present inventors tried to confirm whether cancer may be treated by suppressing an increase in expression at a protein level of the vimentin gene overexpressed in cancer cells. Accordingly, the present inventors designed 3 types of shRNAs to target nucleotide sequences at positions 1447 to 1467 (target #1), 1290 to 1310 (target #2), and 1132 to 1152 (target #3) in a vimentin mRNA (Human vimentin mRNA [NM_003380]) sequence for suppressing vimentin expression, respectively, and confirmed an effect of inhibiting the vimentin expression, and confirmed the expression of CDH1 and CDH2, epithelial-mesenchymal transition-related factors and the expression level of PD-L1 as an immune evasion-related factor by treatment in cancer cells with metastasis induced by TGF-β. As a result, vimentin shRNA #1 was most effective in inhibiting the expression of vimentin, and the expression of CDH1, CDH2, and PD-L1 was significantly reduced in lung cancer cells induced to suppress vimentin expression by such shRNA #1. In addition, it was found that the suppression of vimentin expression by vimentin shRNA inhibits the expression of epithelial-mesenchymal transition-related factors in an environment of cancer metastasis by TGF-β treatment (Example 8).

Figure 6A:
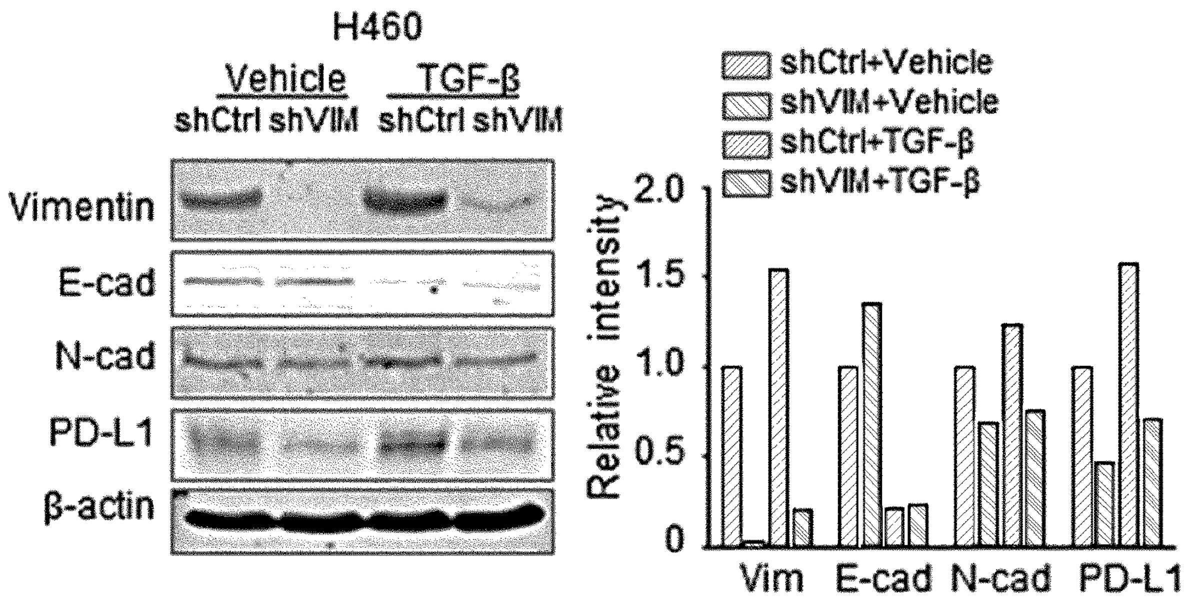
FIGS. 6A to 6J are results of observing changes in epithelial-mesenchymal transition markers and immune evasion factors, and changes in migration and invasion of cancer when lung cancer cells are treated with vimentin shRNA, a substance that inhibits vimentin mRNA expression.
Figure 6B:
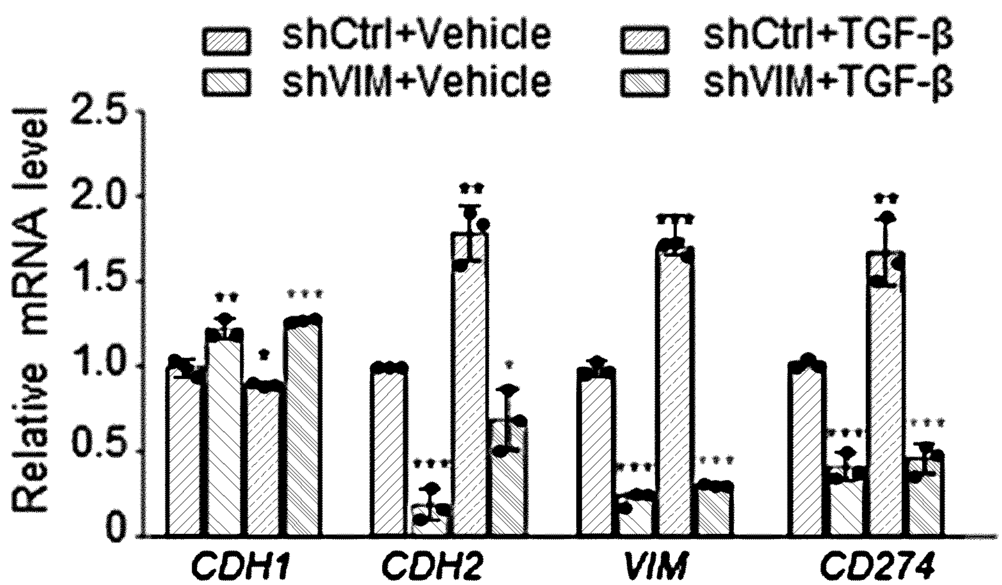
Figure 6C:
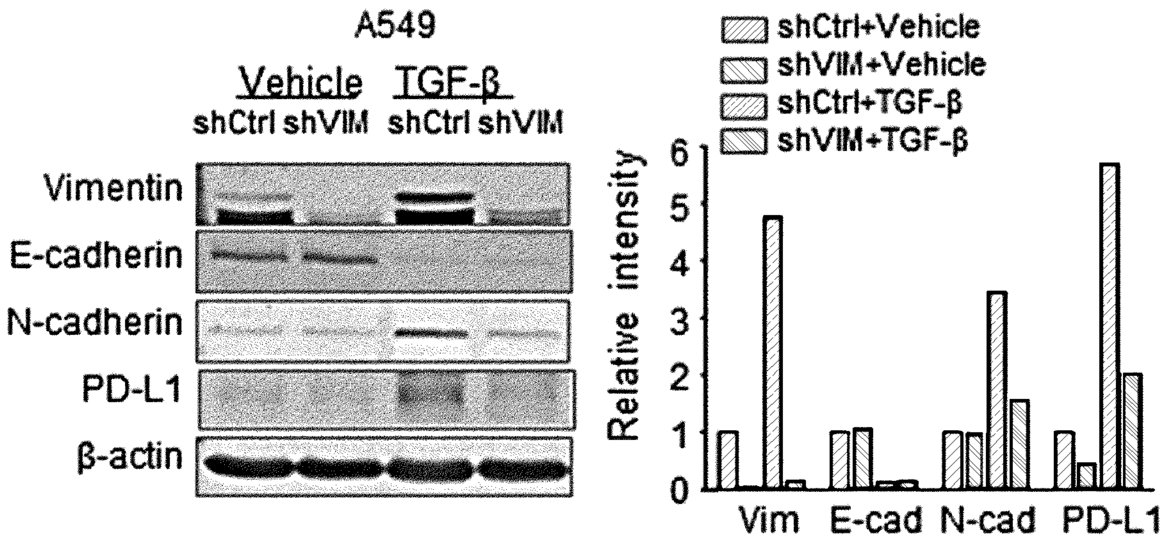
Figure 6D:
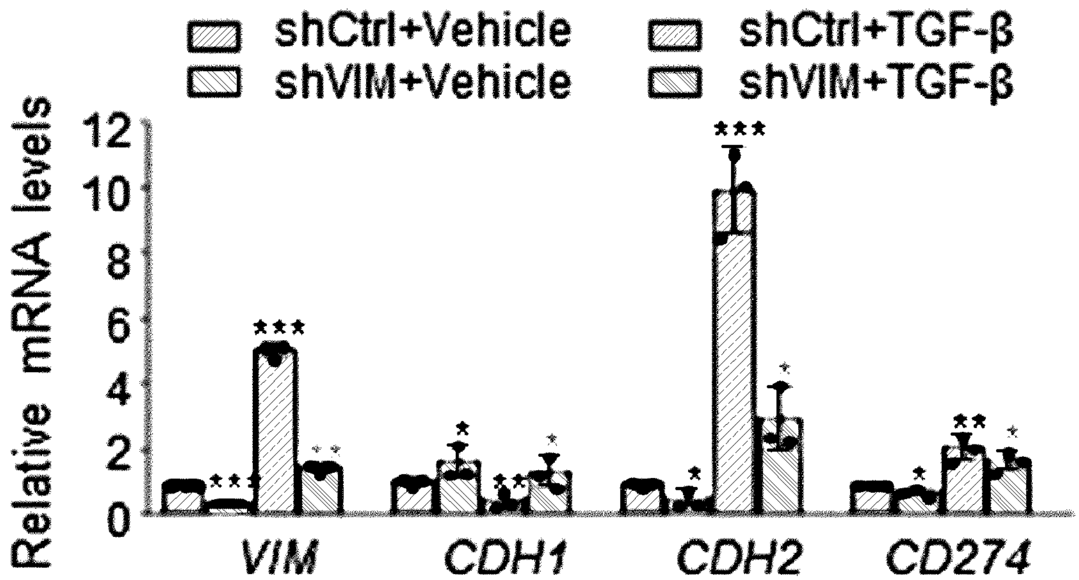
Figure 6E:
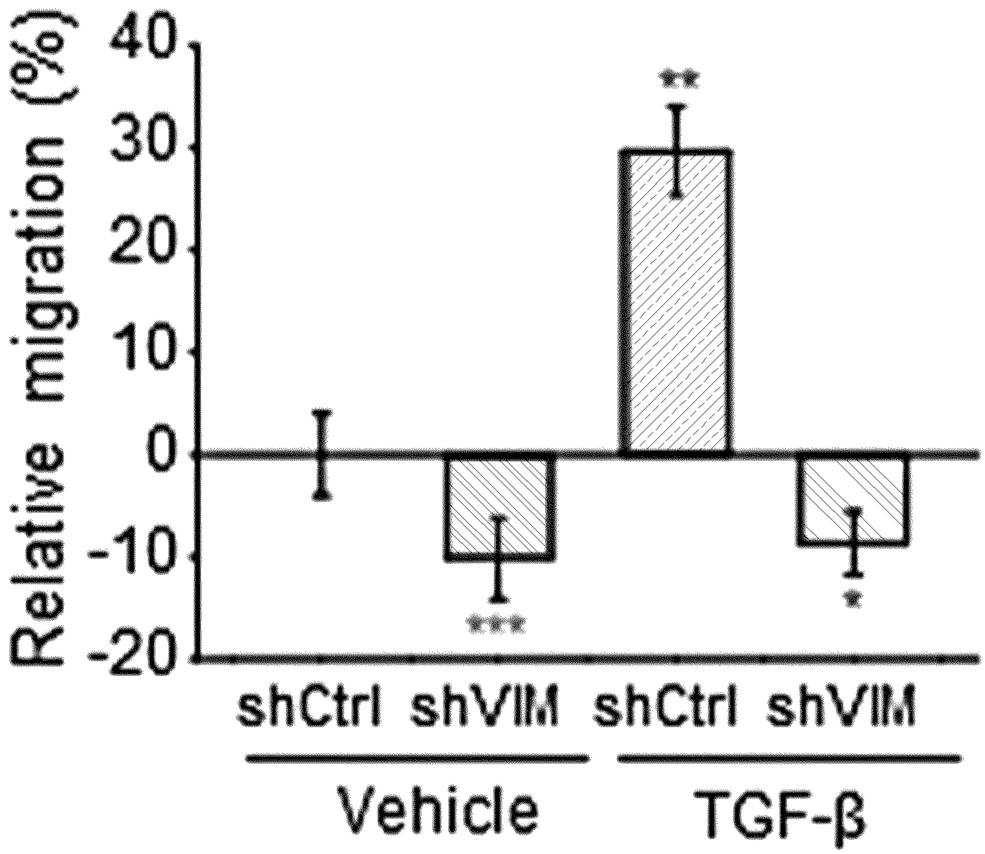

Accordingly, shRNA #1 was selected as shRNA for reducing the expression of vimentin, and lung cancer cells (NCI-H460) were infected with lentivirus expressing the shRNA #1, and then migration assay was performed for 72 hours (FIG. 6E). As a result, when vimentin shRNA was expressed in lung cancer cells, it was observed that the relative metastasis of cells was reduced to about-10% or less at 72 hours. In addition, it was observed that the metastasis of cancer cells was reduced to about-8% or less in a vimentin shRNA expression group even under a condition of inducing cancer metastasis treated with TGF-β at the same time. It was found that when shRNA that inhibited the mRNA expression of vimentin was expressed, a remarkable cancer metastasis inhibitory effect was shown even under the condition of inducing cancer metastasis treated with TGF-β along with the metastasis of cancer cells themselves (Example 9).

In addition, in the present disclosure, the invasion of cancer cells was observed using a three-dimensional transwell culture system made of matrigel in order to confirm an effect of the selected shRNA on the invasion of cancer cells through specific experiments. In the case of invaded cells, the degree of invaded cells could be observed by directly counting the number of stained cells after crystal violet staining. In the case of lung cancer cells treated with TGF-β, which was a positive control group, it was observed that about 15 times more cells were invaded than the control group. In the case of cells expressing Vimentin shRNA, it was observed that invasion was reduced compared to the control group. In addition, in the case of cells expressing vimentin shRNA in cancer metastasis conditions treated with TGF-β, it was observed that invasion was reduced by about 30 times compared to lung cancer cells treated with TGF-β, which was a positive control group. It was found that when shRNA that inhibited the mRNA expression of vimentin was expressed, the invasion of cancer cells was effectively inhibited even under the condition of inducing cancer metastasis treated with TGF-β along with the invasion of cancer cells themselves (Example 10).

Figure 6F:
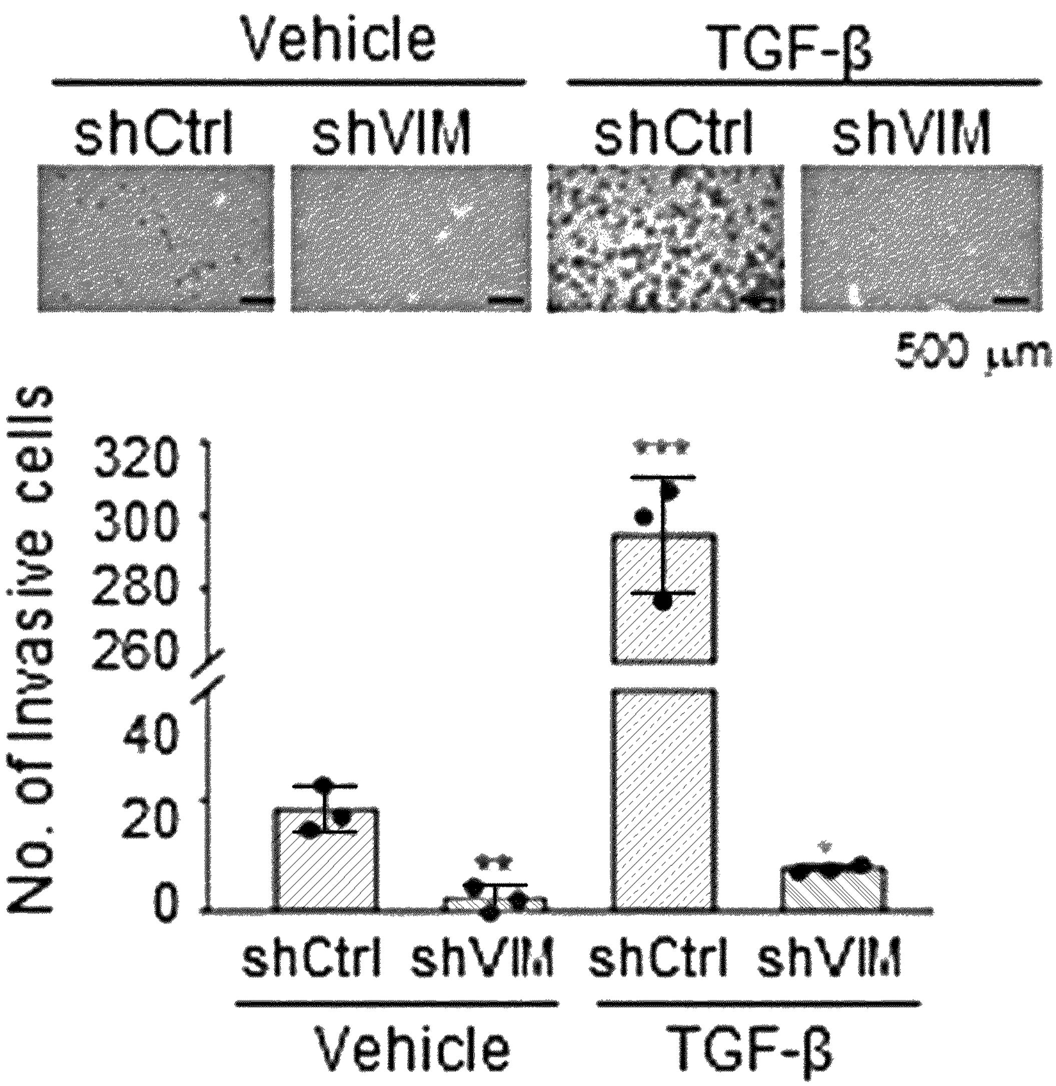
Figure 6G:
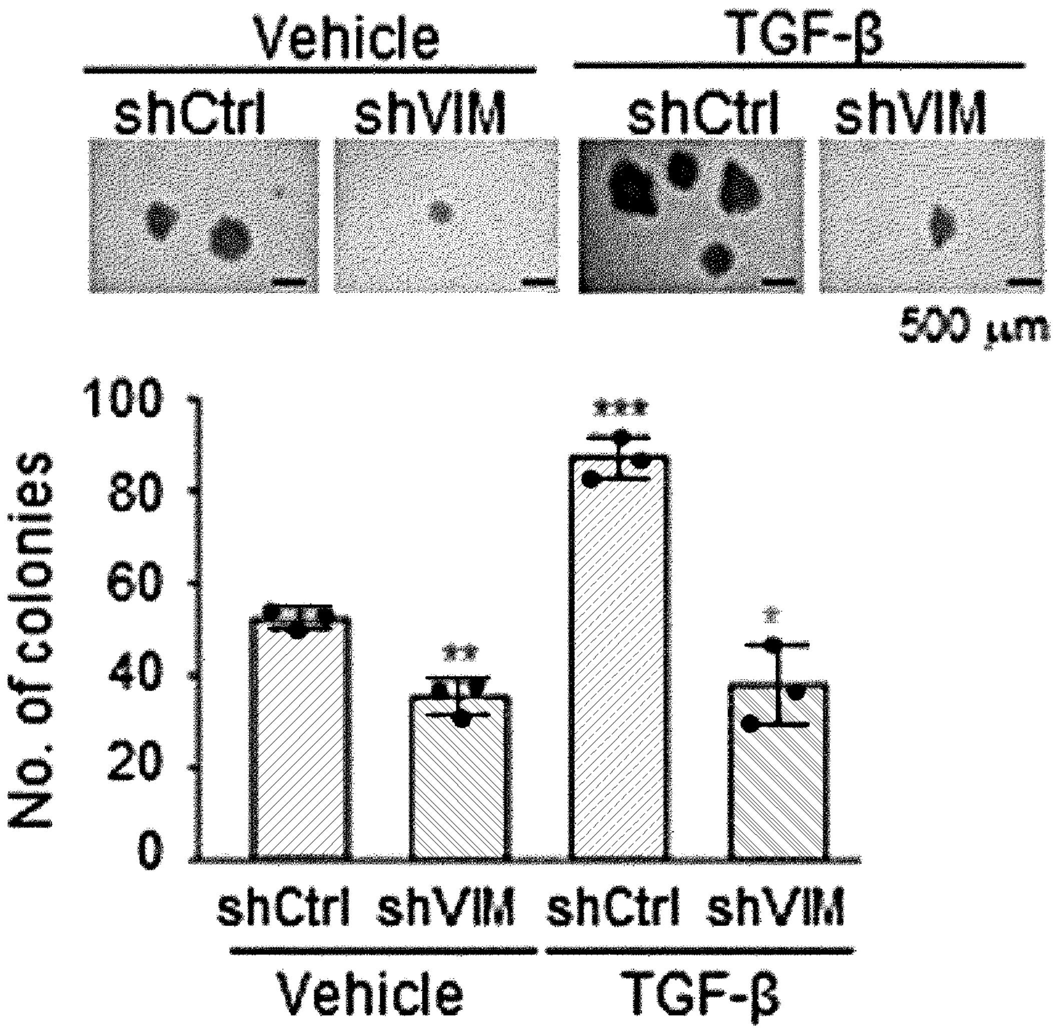

In addition, in the present disclosure, a colony formation assay was conducted to confirm an effect of vimentin shRNA on a tumorigenesis inhibitory effect of lung cancer cells with a lentivirus for expressing vimentin shRNA selected through specific experiments (FIG. 6G). As a result of the study, tumors, which were cancer cell masses, were formed about twice more than the control group by TGF-β treatment, which was a positive control group, and it was observed that tumorigenesis was reduced compared to the control group when vimentin shRNA was expressed. In addition, it was observed that tumorigenesis was reduced in a vimentin shRNA expression group compared to the control group or the positive control group even under the condition of inducing cancer metastasis treated with TGF-β. It was found that when shRNA that inhibited the mRNA expression of vimentin was expressed, a remarkable tumorigenesis inhibitory effect was shown even under the condition of inducing cancer metastasis treated with TGF-β along with the tumorigenesis of cancer cells themselves (Example 11).

Accordingly, the present disclosure provides a pharmaceutical composition for preventing or treating cancer including shRNA for inhibiting vimentin expression and/or a vector expressing the shRNA.

Then, the present inventors tried to confirm an effect on the migration and invasion of cancer cells by simultaneously expressing the shRNA capable of reducing the migration and invasion of cancer and the aforementioned vimentin mutant in cancer cells. Meanwhile, the present inventors confirmed the migration and invasion by simultaneously expressing shRNA and a vimentin phosphorylated mutant in cancer cells in order to confirm simultaneously an effect of the phosphorylation of vimentin on the migration and invasion of cells under conditions of inhibiting the expression of vimentin by shRNA. As a result, it may be confirmed that each vimentin mutant is well expressed under the conditions of inhibiting the expression of vimentin by shRNA, and the phosphorylated vimentin increases the migration and invasion of cells under the conditions of inhibiting the expression of vimentin, so that the phosphorylation of vimentin has a strong promoting effect on the invasion of cancer cells. Therefore, it may be seen that when the inhibition of the vimentin expression is performed simultaneously with the inhibition of the vimentin phosphorylation by the vimentin mutant, the invasion and migration of cancer cells are significantly reduced as compared to when the inhibition is performed independently to prevent the occurrence of metastatic cancer (Example 12).

Accordingly, the present disclosure may provide a non-phosphorylated vimentin mutant and shRNA for inhibiting the vimentin expression as anticancer agents.

The vimentin shRNA and the vimentin mutant in the anticancer composition of the present disclosure may be provided to be included in a vector for intracellular expression, the vector may be loaded and provided into one vector or separate vectors, and when provided as separate vectors, the vector may be used for the prevention or treatment of cancer by administering the vectors to a subject simultaneously or sequentially.

The vimentin shRNA and the vimentin mutant of the present disclosure may be included in a delivery vehicle enabling efficient introduction into cells. The delivery vehicle is desirably a vector, and both a viral vector and a non-viral vector may be used. A virus delivery mechanism includes lentivirus, retrovirus, adenovirus, herpes virus, avipox virus, and the like, but is not limited thereto. The non-viral delivery mechanism may include lipid mediated transfection, liposomes, immunoliposomes, lipofectins, cationic surface amphiphiles, and combinations thereof. In the present disclosure, the lentivirus used as a viral vector for delivery of vimentin shRNA and mutants is a type of retrovirus, and is characterized by infecting non-dividing cells as well as dividing cells due to the nucleophilicity of a pre-integration complex (viral "shell") that enables active introduction into a nucleopore or complete nuclear membrane.

Accordingly, the present disclosure provides a recombinant vector including a gene encoding the vimentin mutation, and the vector is provided as a viral vector and may be used as an anticancer agent based on gene therapy.

The vimentin shRNA of the present disclosure is an oligonucleotide having a sequence complementary to a specific target (#1 to 3) region of the vimentin gene, and refers to shRNA for inhibiting the vimentin expression. The shRNA of the present disclosure may be isolated or prepared using standard molecular biology techniques, such as chemical synthesis or recombinant methods, or used with commercially available shRNAs, and may be prepared and used using genetic engineering methods.

In the present disclosure, the mutant means that one or more amino acids constituting the vimentin protein are substituted, and unless otherwise stated, in the present specification, a mutant having an anticancer effect by reducing the migration and invasion of cancer cells and tumorigenesis means that the T327 and/or S339 amino acids of vimentin are substituted.

As used herein, the term 'anticancer' refers to an action of inhibiting or killing the proliferation of cancer cells and an action of inhibiting or blocking the metastasis of cancer cells, and refers to both prevention and treatment of cancer, and may be used interchangeably therewith. As used herein, the term 'prevention' refers to any action that inhibits cancer formation or delays the onset of cancer by administration of the composition, and the 'treatment' refers to any action that improves or beneficially changes the symptoms of the disease by administration of the composition.

The anticancer agent of the present disclosure may further include other substances known to inhibit phosphorylation of vimentin or reduce its expression, such as compounds, natural products, novel proteins, etc., in addition to the above-described shRNA and mutants.

In addition, the anticancer agent of the present disclosure may be used for the prevention and treatment of various solid cancers such as colorectal cancer, prostate cancer, breast cancer and stomach cancer, and leukemia with excessive expression of vimentin, and may also be used for the prevention and treatment of metastatic solid cancer caused by metastasis from primary cancer.

The pharmaceutical composition for preventing or treating cancer including the vimentin mutant of the present disclosure and the vector expressing the vimentin mutant may include commonly used excipients, disintegrants, sweeteners, lubricants or flavoring agents, and may be formulated into tablets, capsules, powders, granules, suspensions, emulsions, syrups and other liquids by conventional methods. Specifically, the apoptosis activator of the present disclosure, for oral administration, may be prepared in the form of, for example, troches, lozenges, aqueous or oily suspensions, prepared powders or granules, emulsions, hard or soft capsules, syrups or elixirs. At this time, in order to formulate tablets and capsules, binders such as lactose, saccharose, sorbitol, mannitol, starch, amylopectin, cellulose or gelatin; excipients such as dicalcium phosphate; disintegrants such as corn starch or sweet potato starch; and lubricants such as magnesium stearate, calcium stearate, sodium stearyl fumarate or polyethylene glycol wax may be added. In addition, when formulated into capsules, the apoptosis activator may be prepared by including one or more pharmaceutically acceptable carriers in addition to the above-mentioned substances. For example, the pharmaceutically acceptable carrier may be used by mixing saline, sterile water, a Ringer's solution, buffered saline, a dextrose solution, a maltodextrin solution, glycerol, ethanol, liposomes and one or more of these components, and if necessary, other conventional additives such as antioxidants, buffers, bacteriostats, etc. may be added. In addition, diluents, dispersants, surfactants, binders and lubricants may be additionally added to prepare formulations for injections such as aqueous solutions, suspensions and emulsions, and antibodies or other ligands specific to target cells may be used in combination with the carrier so as to specifically act on target cells. Furthermore, the pharmaceutical composition may be prepared desirably according to each disease or ingredient by using a suitable method of the art, or a method disclosed in the Remington's document (Remington's Pharmaceutical Science, Mack Publishing Company, Easton PA).

The composition of the present disclosure may be administered parenterally, and when administered parenterally, it is desirably administered by intravenous injection, intramuscular injection or intrathoracic injection. In order to be formulated for parenteral administration, the apoptosis-promoting anticancer agent may be mixed in water together with a stabilizer or buffer to be prepared as a solution or suspension, which may be formulated into a unit dosage form in an ampoule or vial.

The dosage is desirably selected according to the absorption rate, inactivation rate and excretion rate of the active ingredients in the body, the age, sex and condition of a patient, and the severity of the disease to be treated, and the anticancer agent for promoting cancer cell death of the present disclosure may be administered in an amount of 1 to 100 mg, desirably 1 to 10 mg per 1 kg of body weight of an adult, once or several times daily.

The present disclosure may have various modifications and various embodiments and specific embodiments will be illustrated in the drawings and described in detail in the detailed description. However, the present disclosure is not limited to specific embodiments, and it should be understood that the present disclosure covers all the modifications, equivalents and replacements within the idea and technical scope of the present disclosure. In describing the present disclosure, if it is determined that a detailed description of related known technologies may obscure the gist of the present disclosure, the detailed description will be omitted.

<Example 1> Clinical Association of Vimentin and Active PLK1 in Metastatic Lung Cancer Cells and Expression Analysis of Vimentin and Active PLK1 in Cancer Metastasis Conditions Induced by TGF-β

Figure 1B:
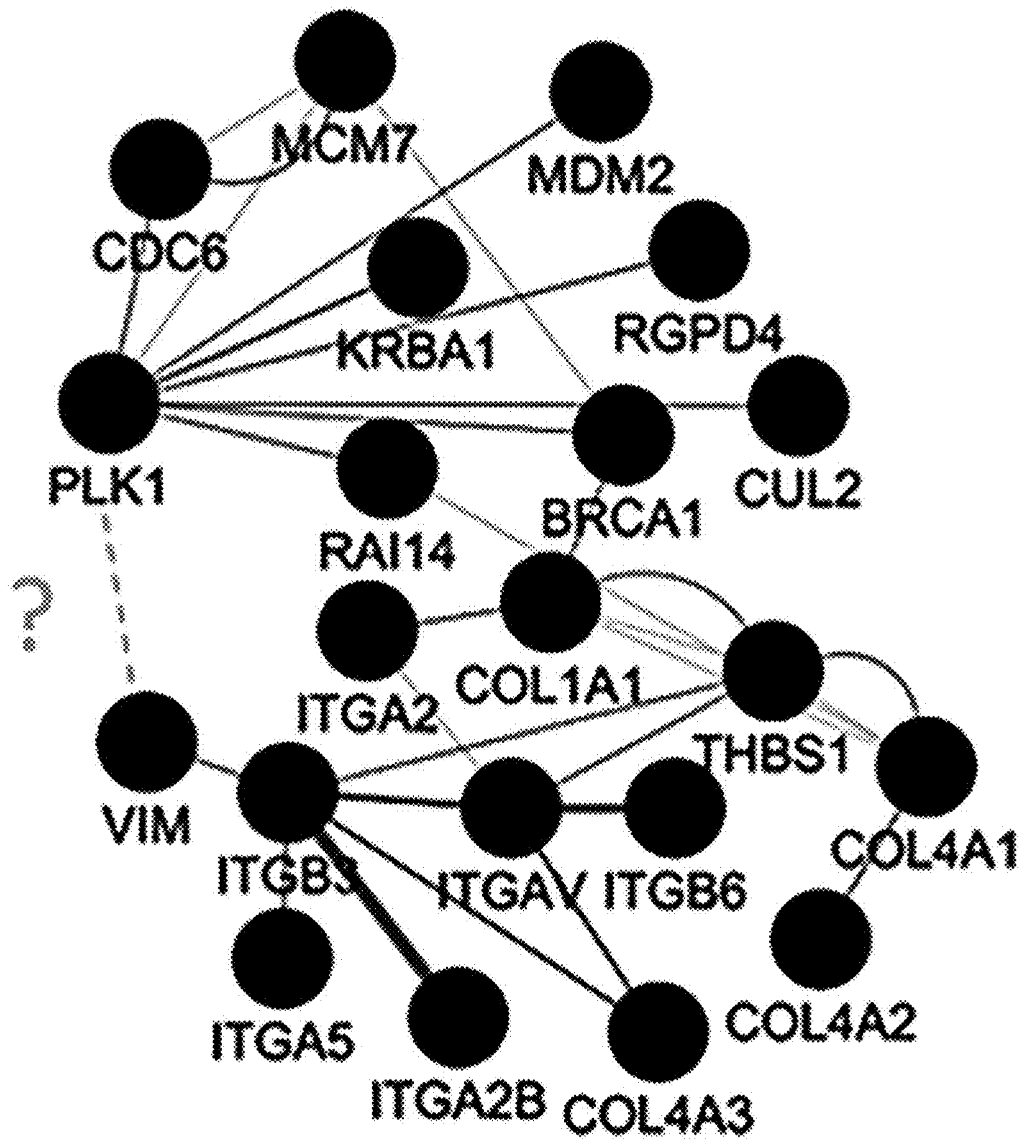

In a recent study (Shin S. B. et al., Oncogene 39 (2020) 767-785), changes in ECM-adhesion-related genes during PLK1-induced cancer metastasis in non-small cell lung cancer cells were observed (FIG. 1A). Vimentin was a major ECM regulator involved in TGF-β-induced cancer metastasis (Liu C. U. et al., Oncotarget 6 (2015) 15966-15983; Mendez M. G. et al., FASEB J 24 (2010) 1838-1851), and a matrix protein phosphorylated by PLK1 during cancer cell invasion (Rizki A. et al., Cancer Res 67 (2007) 11106-11110). However, in the results obtained through analysis of a GeneMANIA database, an interaction network between PLK1 and vimentin could not be confirmed (FIG. 1B). Therefore, this study was conducted to identify the relationship between PLK1 and vimentin.

Figure 1C:
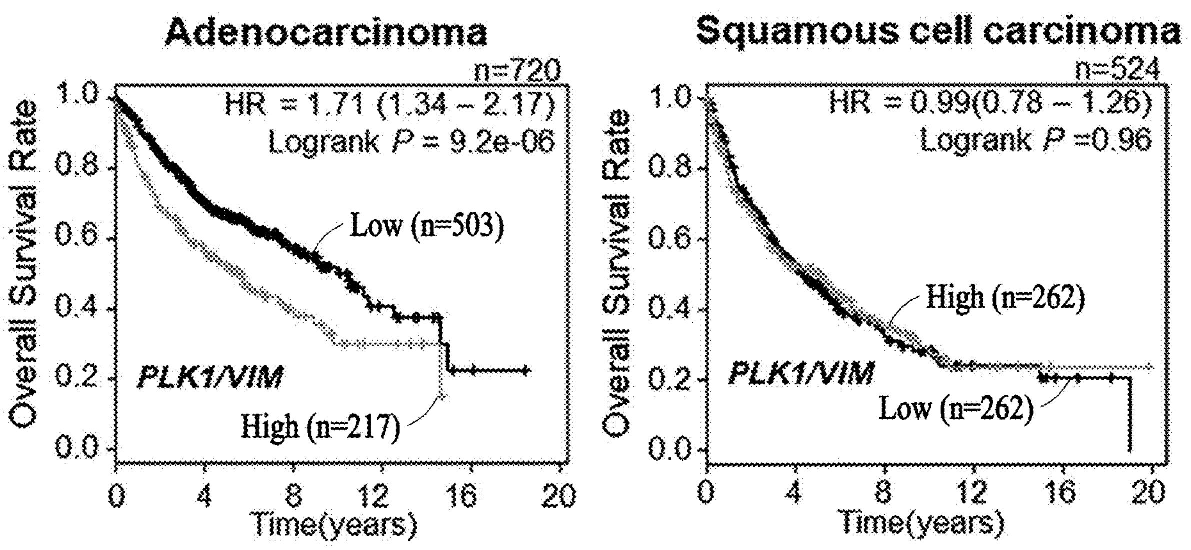
Figure 1D:
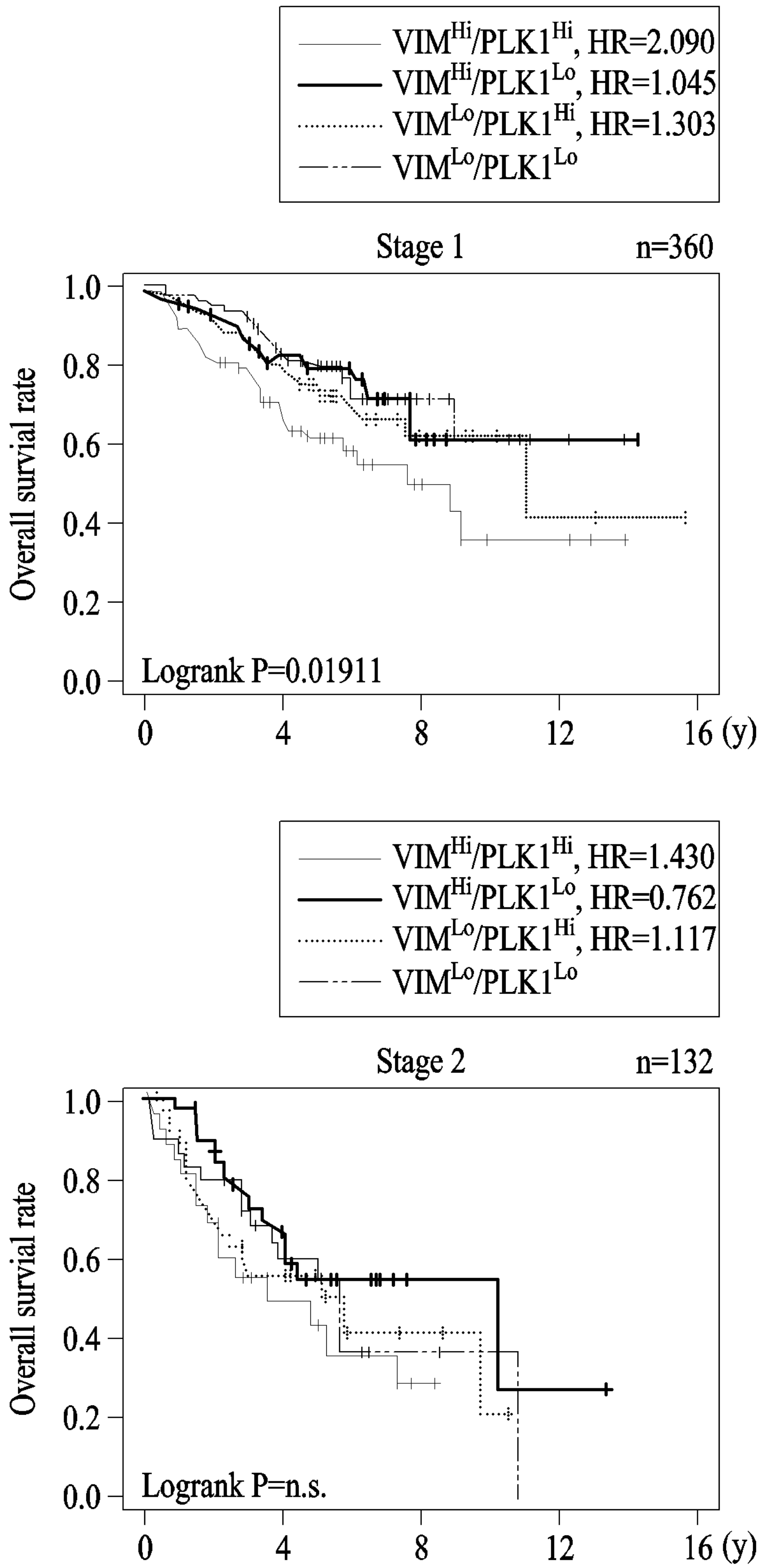

First, in order to confirm the clinical association of vimentin and PLK1, the overall survival rate of patients according to protein expression levels of vimentin and PLK1 in non-small cell lung cancer patients was confirmed through big data analysis (FIG. 1C). First, in adenocarcinoma among non-small cell lung cancers, the survival rate of patients with the high expression of PLK1 and vimentin was significantly lower than that of patients with the low expression of PLK1 and vimentin. However, in squamous cell carcinoma, the association between the survival rate of patients and the expression of PLK1 and vimentin was not observed. In addition, it may be observed that as the stage of cancer progression among lung adenocarcinoma patients was higher, that is, the stage progressed to metastatic cancer, the survival rate of patients with the high expression of PLK1 and vimentin decreased more and more significantly compared to that of patients with the low expression of PLK1 and vimentin (FIG. 1D). As a result, it was confirmed that the association between the expression levels of PLK1 and vimentin and the survival rate of patients in adenocarcinoma among non-small cell lung cancers was confirmed, and in particular, it was confirmed that the expression levels of PLK1 and vimentin were increased in patients with advanced cancer metastasis, and had a great effect on their survival rate.

Figure 1E:
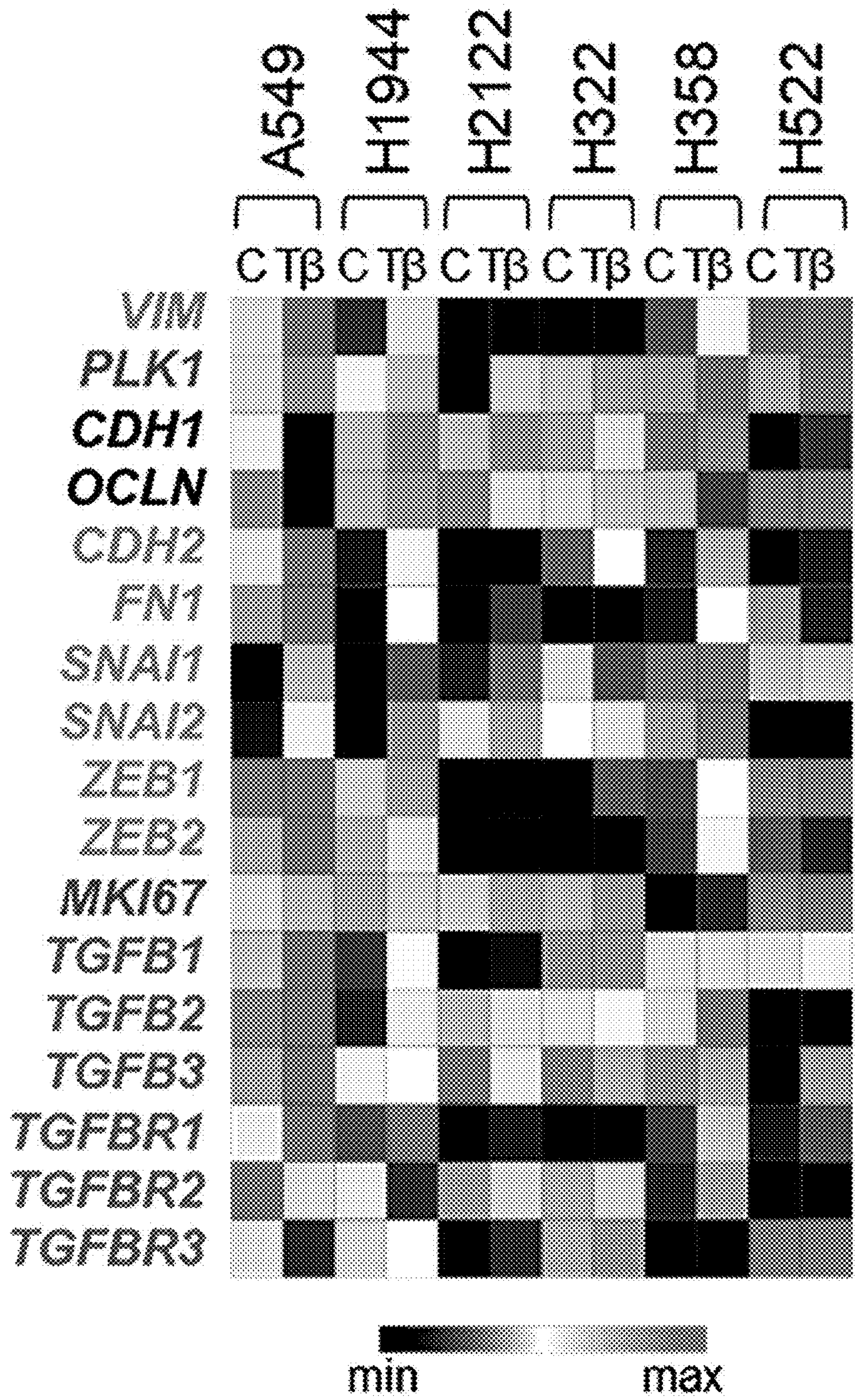

In order to examine the expression of vimentin and PLK1 in metastatic lung cancer, the present inventors constructed a heat map by analyzing microarray data (GSE 114761) under conditions in which cancer metastasis was induced by treating lung cancer cells with TGF-β (FIG. 1E). Through heat map analysis, it was found that the expression of vimentin and PLK1 mRNA was high in lung cancer cells treated with TGF-β under cancer metastasis conditions where mesenchymal transition markers CDH2, SNAI1, and SMAI2 were high, and epithelial markers CDH1 and OCLN were low.

Figure 1F:
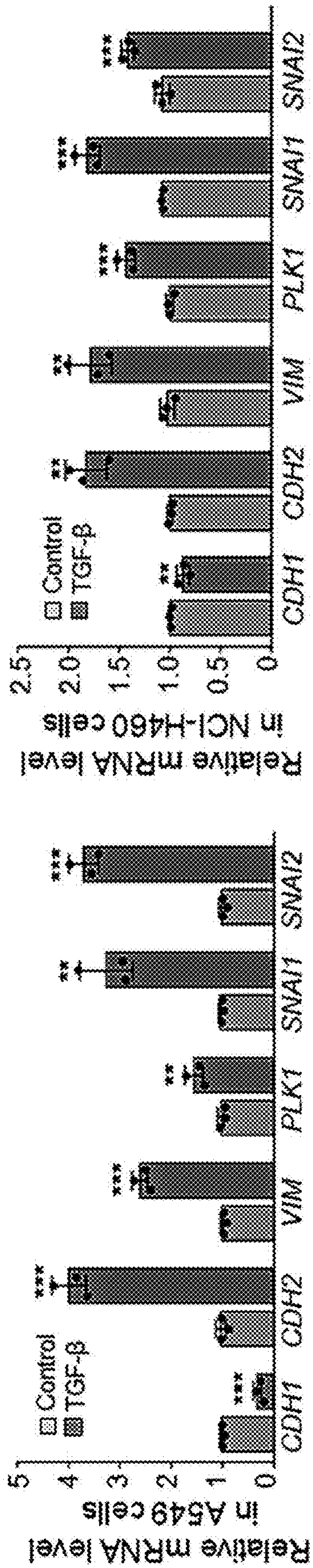
Figure 1G:
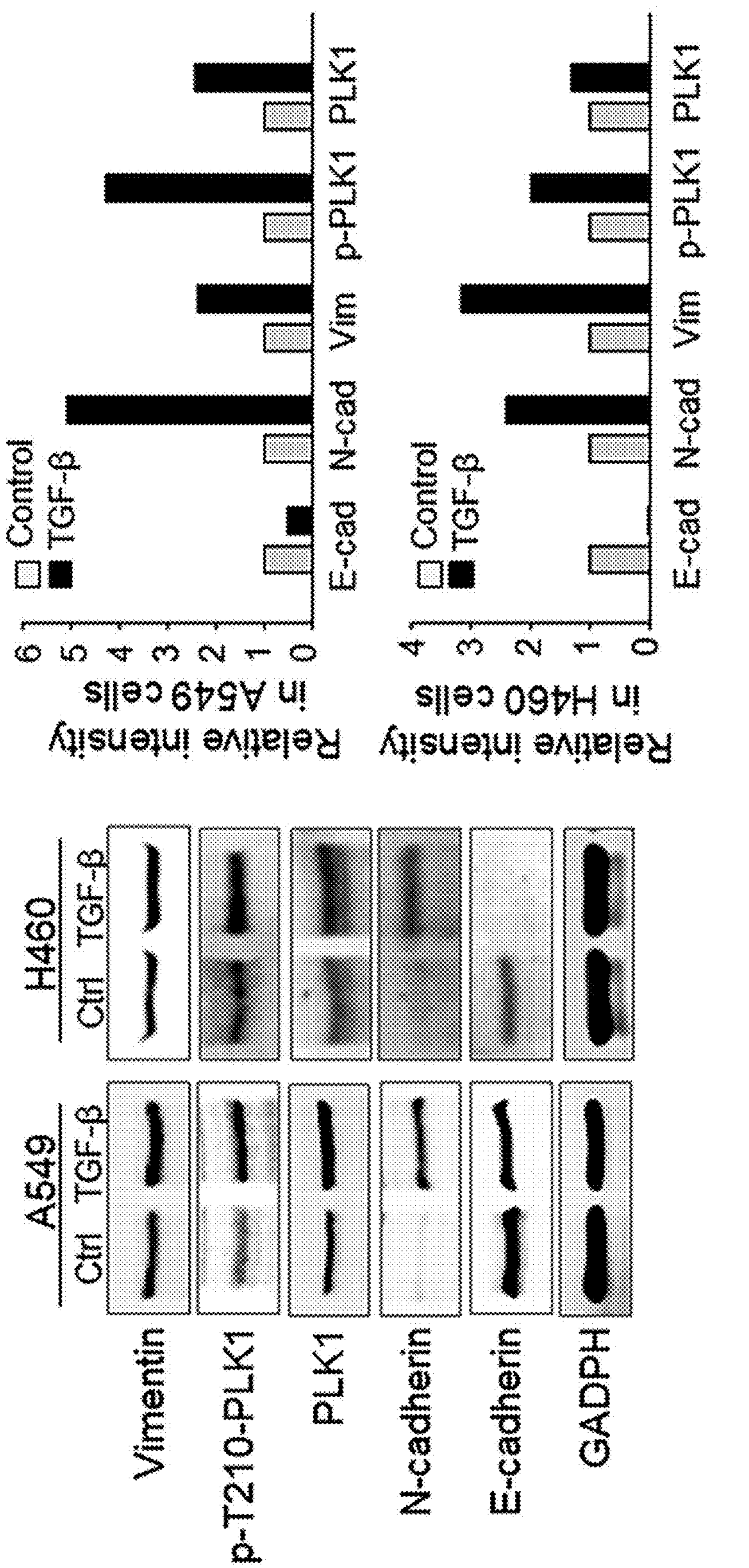
Figure 1H:
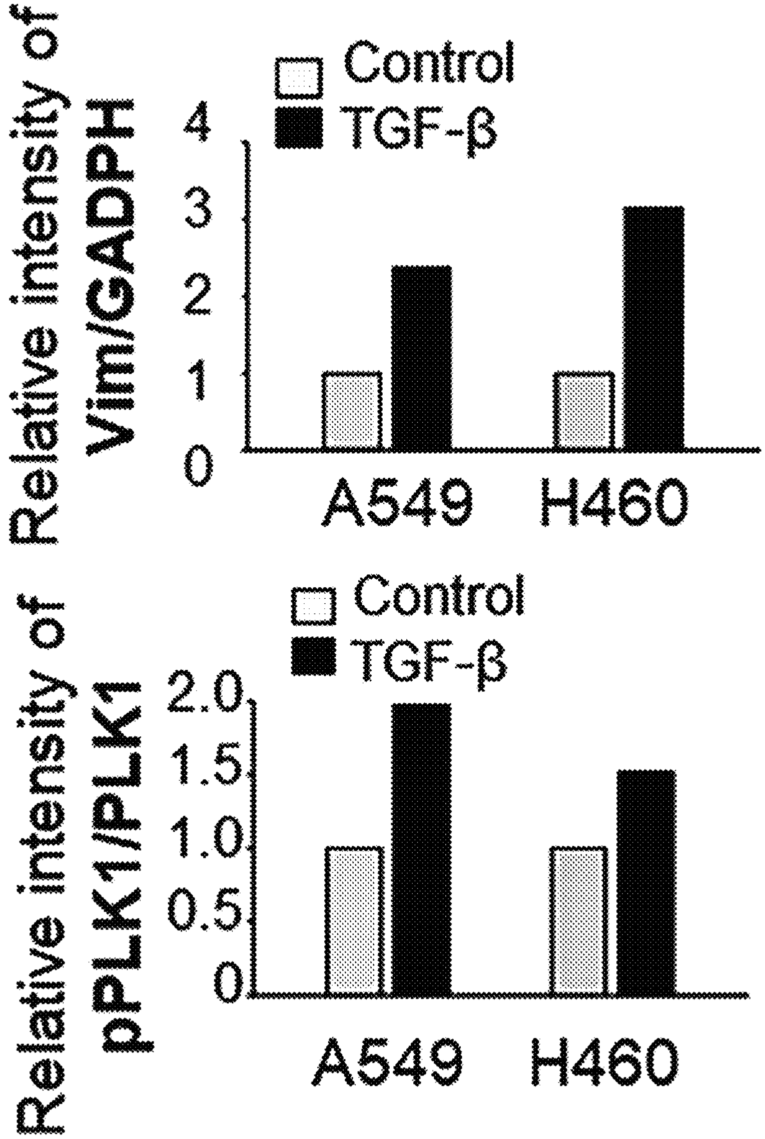

To determine changes in the expression of PLK1 and vimentin and the activation of PLK1 during epithelial-mesenchymal transition of lung cancer, non-small cell lung cancer cell lines A549 and NCI-H460 were treated with TGF-β to induce cancer metastasis, and expression levels of the mRNA and the protein were then analyzed. First, in the group treated with TGF-β, the mRNA expression levels of mesenchymal transition markers CDH2, SNA11, and SNAI2 were increased, and the mRNA expression level of the epithelial marker CDH1 was decreased. In this condition, an increase in the mRNA expression levels of PLK1 and vimentin was observed compared to the control group (FIG. 1F). In addition, the protein levels of vimentin, PLK1, E-cadherin and N-cadherin showed the same results as the mRNA expression levels (FIG. 1G). Additionally, it was observed that the protein expression level of phosphorylated PLK1, which was an activated form, was higher in the TGF-β treated group than in the control group (FIGS. 1G to 1H).

These results suggested that in lung cancer, especially in lung adenocarcinoma, not only the expression of PLK1 and vimentin was high, but also their expression patterns were similar and clinically had correlation.

<Example 2> Confirmation of Phosphorylation of Vimentin by Active PLK1 and New Phosphorylation Sites in Metastatic Lung Cancer Cells Induced by TGF-β

Figure 2A:
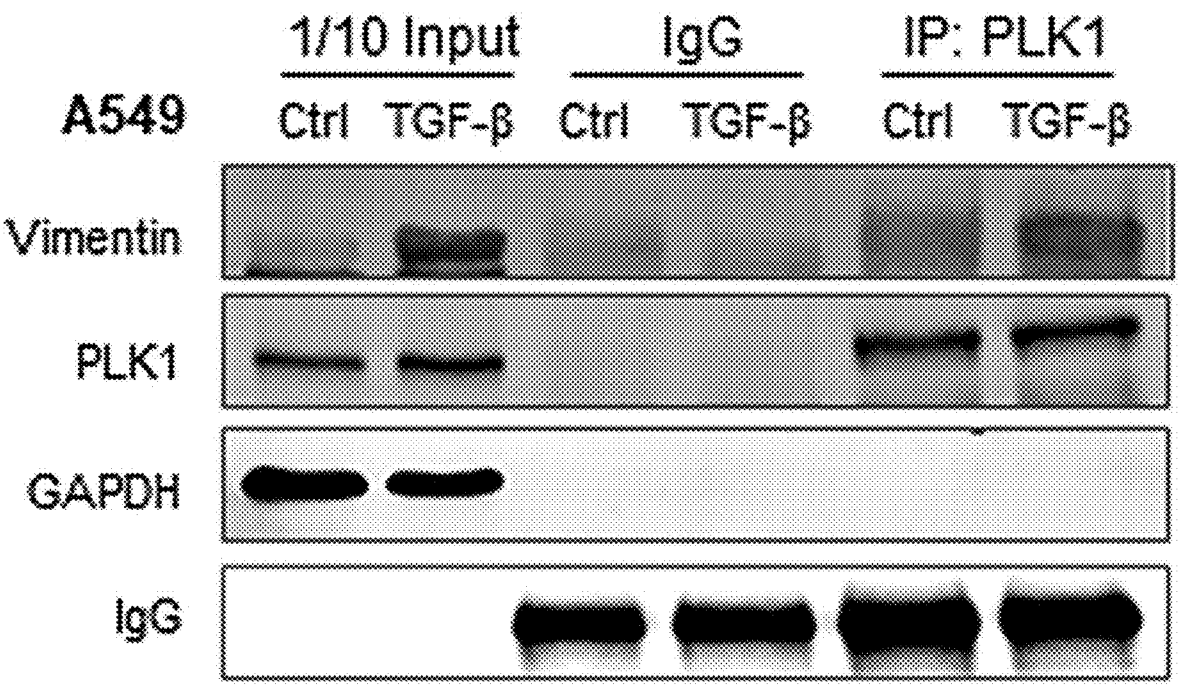
FIGS. 2A to 2G are results of analyzing phosphorylation and phosphorylation sites of vimentin by a PLK1 activation type.
Figure 2B:
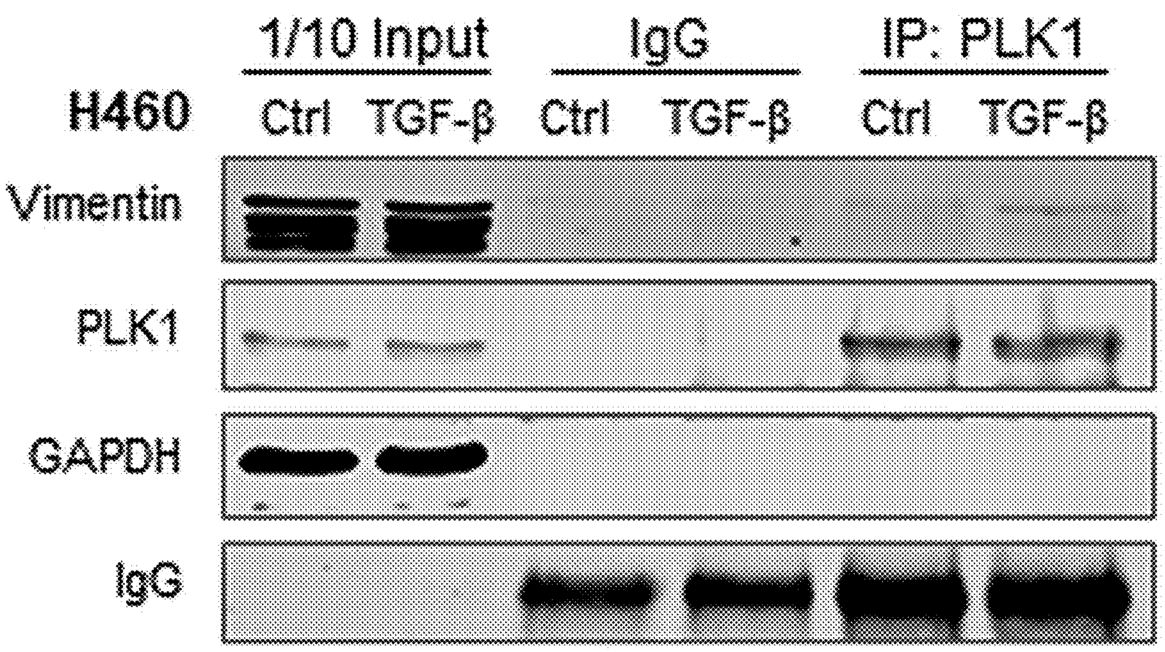

Immunoprecipitation was performed to study the interaction between PLK1 and vimentin in cancer metastasis conditions induced by TGF-β treatment. The PLK1 protein was precipitated with agarose beads and a PLK1 antibody and analyzed by immunoblotting. Vimentin was also combined with PLK1 even in the control group, and the binding between PLK1 and vimentin was increased in the experimental group in which cancer metastasis was induced by TGF-β (FIGS. 2A and 2B). These results suggest that the interaction between PLK1 and vimentin is more active in cancer cells during metastasis.

Figure 2C:
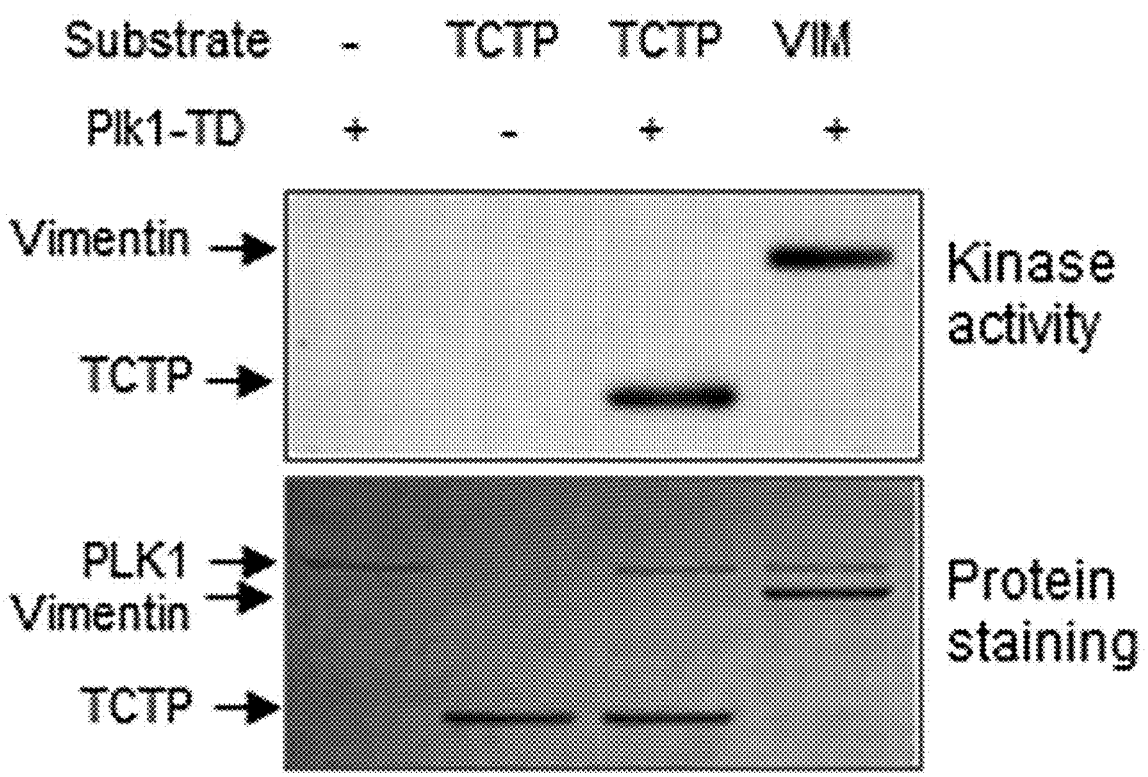

Next, a phosphatase reaction method was performed to analyze the interaction method of the two proteins. As a method of proving that serine/threonine phosphatase PLK1 phosphorylated vimentin as a substrate, purified vimentin wild type and active PLK1-T210D were treated and reacted with radiolabeled r32-P-ATP and analyzed. Vimentin was strongly phosphorylated by active PLK1-TD at a level similar to that of TCTP, a positive control group (FIG. 2C).

Figure 2D:
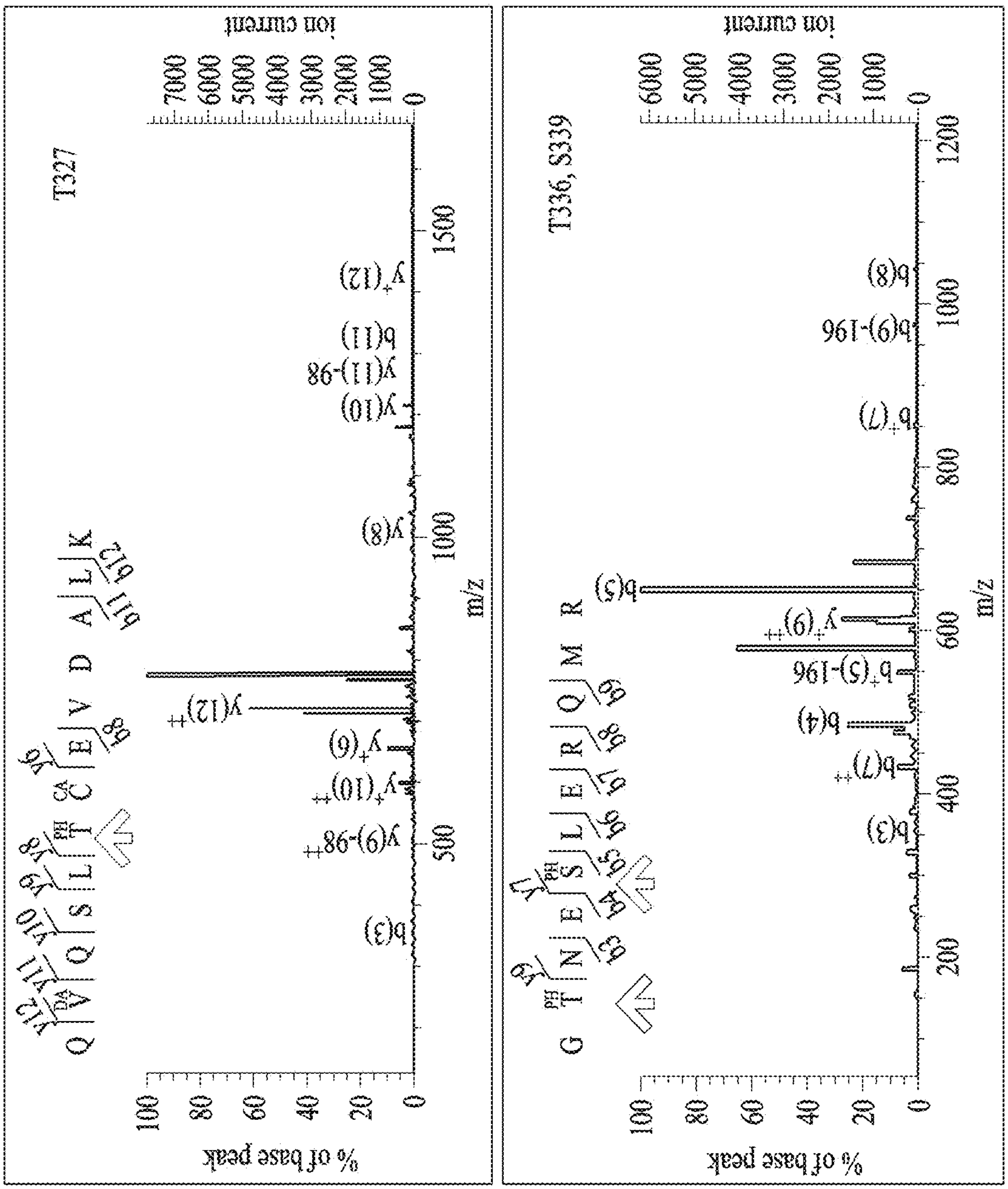
Figure 2E:
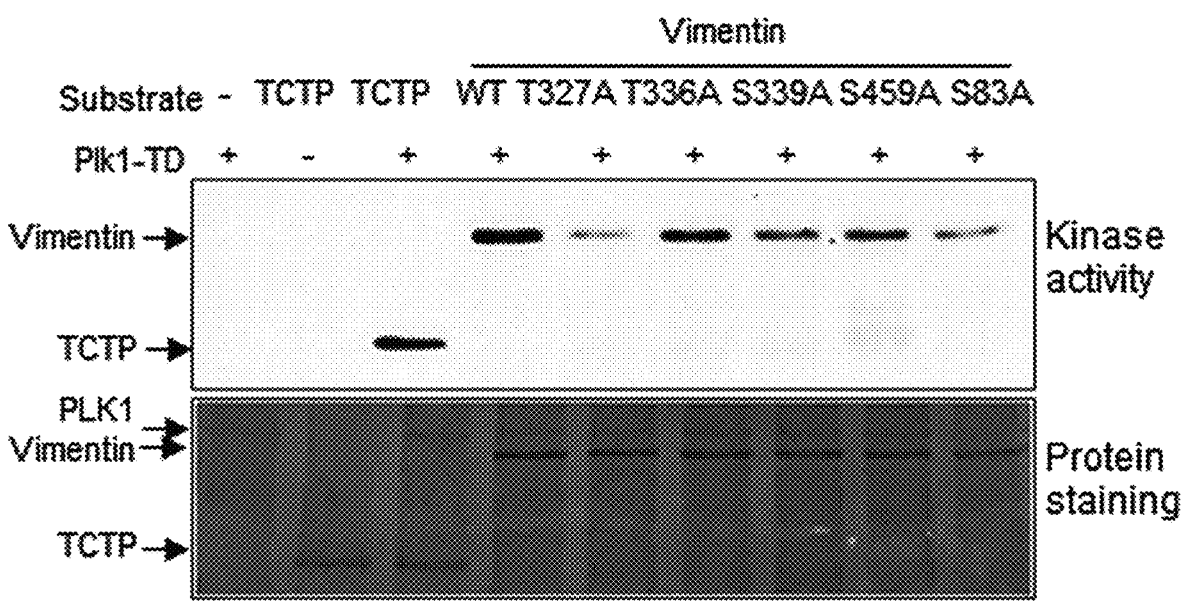

Liquid chromatography mass spectrometry was performed to find the phosphorylation site of vimentin by PLK1. By the assay, Thr-327, Thr-336, and Ser-339 of vimentin were predicted as sites to be phosphorylated by PLK1 (FIG. 2D). Three predicted phosphorylation sites of vimentin and two sites reported to phosphorylate vimentin by PLK1 were constructed as dephosphorylated mutants substituted with alanine using a site-specific mutation substitution method.

The constructed mutants were produced as GST-labeled proteins, purified, and subjected to a phosphatase reaction method. Among the three predicted phosphorylation sites of vimentin, the phosphorylation levels of alanine mutations of Thr-327 and Ser-339 significantly decreased compared to the wild type (FIG. 1E). As these study results, it could be seen that PLK1 interacted with vimentin through phosphorylation of Thr-327 and Ser-339.

Figure 2F:
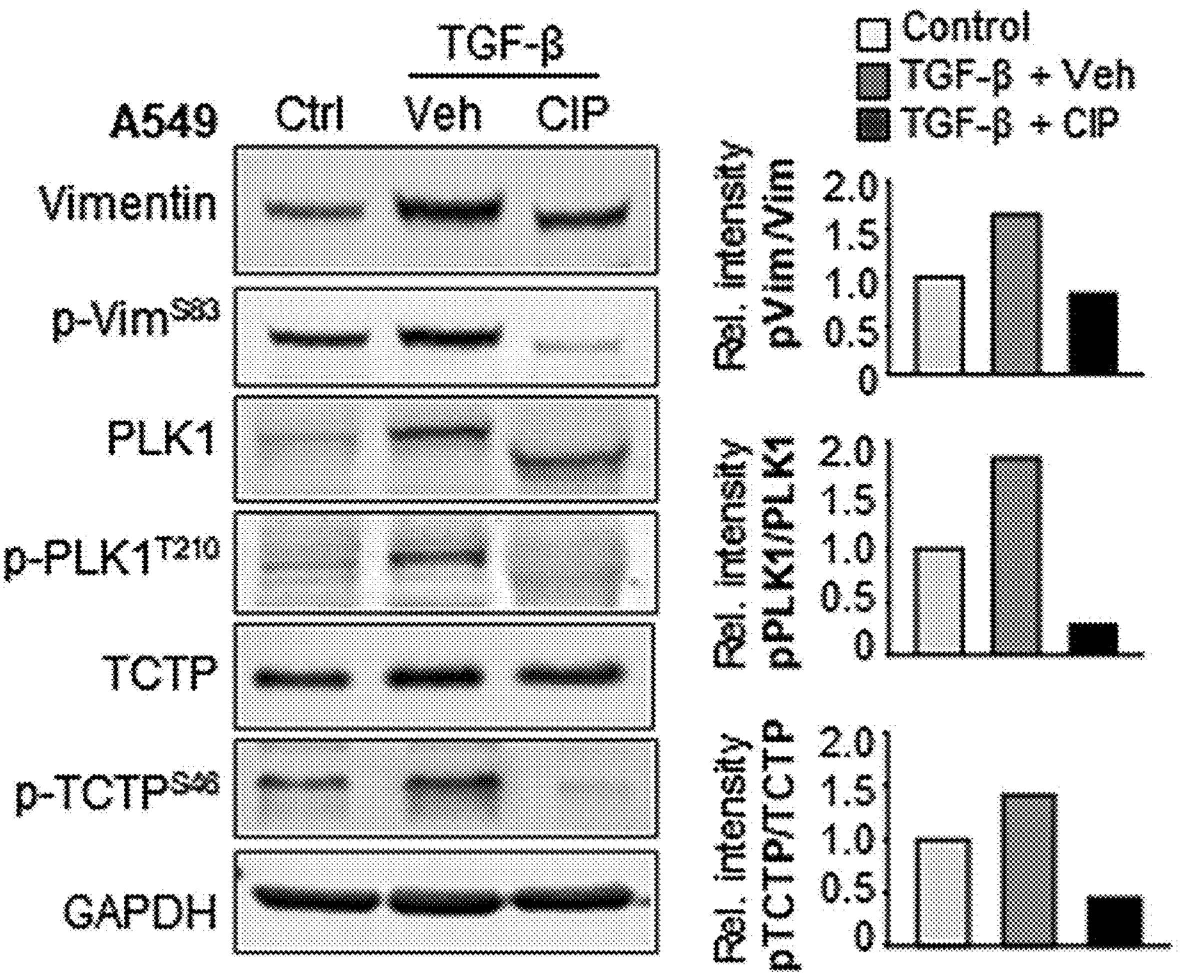
Figure 2G:
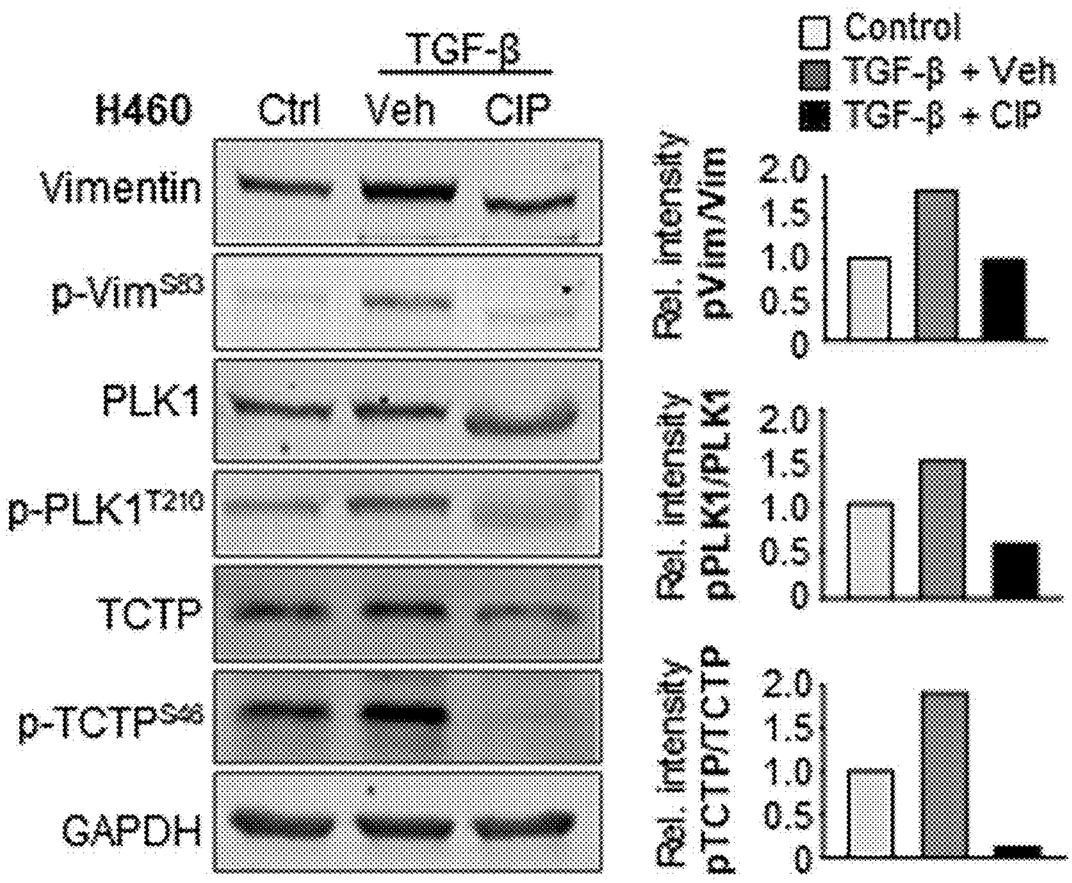

In addition, it was observed that the expression levels of phosphorylated vimentin and PLK1 decreased after treatment with phosphatase in lung cancer cell lines A549 and NCI-H460, which were treated with TGF-β to induce cancer metastasis (FIGS. 2F to 2G). From the results, it may be seen that vimentin and PLK1 are phosphorylated during cancer metastasis induced by TGF-β treatment.

<Example 3> Construction of Lentiviral System for Expression of Phosphorylated and Non-Phosphorylated Point Mutants of Vimentin To construct a lentivirus system for the expression of phosphorylation and non-phosphorylation genes of vimentin, the present inventors cut pLVX-TRE3G-eRFP with Mlu1 and Apa1, a vimentin wild-type (WT) plasmid was amplified with PCR using the primer of 5'-ACGGGGCC-CATGTCCACCAGGTCCGTGTC-3' (forward primer) and 5'-ACGACGCGTTTATTCAAGGTCATCGTGA-3' (reverse primer), and then cut with Mlu1 and Apa1, and subcloned in a vector pLVX-TRE3G-eRFP. To construct a lentivirus system, pCMV-VSV.G, pCMV-48.2, and pLVX-TRE3G-eRFP-Target or pLVX-Tet3G DNA were transfected in HEK293 cells to express lentivirus, and then the virus was collected to be used for cancer cells. After transfection, a virus culture medium was collected at 12-hour intervals up to 72 hours, and the culture medium was filtered with a 0.2 mm filter and centrifuged at 17000 rpm, 4° C., and 90 minutes. The supernatant was discarded, and the collected viruses was collected with TNE Buffer, stored at 4° C., and used for cancer cell infection from the next day.

<Example 4> Evaluation of Epithelial-Mesenchymal Transition Effect after Selection of Cells for Expressing Active and Inactive Genes of Vimentin Using Lentivirus In order to examine an effect of a vimentin protein containing point mutations on regulation of epithelial-mesenchymal transition in cancer cells, to infect lung cancer cells with lentivirus expressing phosphorylated and non-phosphorylated point mutants of vimentin, cancer cells were cultured as follows.

In order to construct a stable cell line expressing a wild type and phosphorylated and non-phosphorylated point mutants of vimentin in lung cancer cells NCI-H460, first, pLVX-Tet3G-expressing lentivirus was infected, and treated with G418 for 5 days to select infected cells. The selected NCI-H460Tet3G cells were infected with lentiviruses expressing the wild type and phosphorylated point mutants S339E, T327E, S83E, and S459E, and non-phosphorylated point mutants S339A, T327A, S83A, and S459A of vimentin, and then treated with puromycin for 48 hours to construct a stabilized cell line. The constructed cells were treated with 1 μg/ml doxycycline to induce the expression of the wild type and the phosphorylated and non-phosphorylated point mutants of vimentin, and then whether each point mutant of vimentin was expressed well was confirmed through mRNA expression level and protein expression level. As illustrated in FIGS. 3A and 3B, whether the wild type and each point mutant of vimentin were expressed well was confirmed through the mRNA expression level and the protein expression level. Excluding a phosphorylation site S459, it was observed that the expression of N-cadherin was higher in lung cancer cells expressing phosphorylated vimentin than in cells expressing non-phosphorylated vimentin. In addition, as a result of confirming whether the expression of phosphorylated and non-phosphorylated point mutants of vimentin affected cell proliferation, it was observed that the expression did not significantly affect the cell proliferation (FIG. 3C).

As these results, it was suggested that the phosphorylation of vimentin promoted epithelial-mesenchymal transition in lung cancer cells.

<Example 5> Evaluation of Metastatic Promotion and Inhibition Effects by Proteins Containing Phosphorylated and Non-Phosphorylated Point Mutations of Vimentin Migration assay was performed to observe an effect of these point mutants on the migration of cancer cells in lung cancer cells NCI-H460 expressing the wild type, phosphorylated and non-phosphorylated point mutant proteins of vimentin.

Specifically, $5\times10^4$ lung cancer cells NCI-H460 expressing each of the wild type, phosphorylated and non-phosphorylated point mutant proteins of vimentin were dispensed into a 8.0 μm, 24 well insert and a medium containing 10% serum (FBS) was dispensed into a 24-well plate and added with the insert. In the case of a positive control group, 0.5 ml of RPMI 1640 (10% FBS) containing 2.5 ng/ml TGF-β was dispensed and used. After 72 hours of cell dispensation, 500 μl of 4% paraformaldehyde was dispensed, washed three times with 1×PBS, and stained with a 0.05% crystal-violet solution for 5 minutes. After 5 minutes, the cells were washed 5 times with 1×PBS, and the staining intensity was measured using an Odyssey infrared imaging system. When the staining intensity of the control group was 1, a relative staining intensity in each experimental group was calculated and a graph was displayed.

As a result of the study, it may be observed that in the experimental group expressing the phosphorylated point mutant protein of vimentin, the staining intensity level increased up to 5 times compared with the control group, similar to or higher than the positive control group, a TGF-β treated group, and the staining intensity of the experimental group of the non-phosphorylated point mutant was relatively lower than that of the phosphorylated point mutant of vimentin (FIGS. 3D to 3E). However, it was observed that the S459 phosphorylated mutant of vimentin did not affect the migration of cancer cells. As a result, it was found that the vimentin phosphorylated point mutant promoted the migration of lung cancer cells, whereas the vimentin non-phosphorylated point mutant had an excellent effect of inhibiting the migration of lung cancer cells.

<Example 6> Evaluation of Invasion Promotion and Inhibition Effects by Proteins Containing Phosphorylation Sites and Non-Phosphorylated Point Mutations of Vimentin An invasion assay was performed using a matrigel to observe an effect of these point mutants on the invasion of cancer cells in lung cancer cells NCI-H460 expressing the wild type, and the phosphorylated and non-phosphorylated point mutant proteins of vimentin.

Specifically, the matrigel was completely dissolved at 4° C. for 16 to 20 hours, and then diluted with cold serum free RPMI 1640 (4° C.) to become a concentration of 1 mg/ml. 100 μl of a matrigel mixture (1 mg/ml) was put into an 8.0 μm, 24 well insert and solidified in a 37° C. incubator for 12 to 20 hours. The lung cancer cells NCI-H460 expressing each of the wild type, phosphorylated and non-phosphorylated point mutant proteins of vimentin in the solidified matrigel insert were diluted in serum free RPMI 1640 (36° C.) at a cell count of $1\times10^5$ cells/well and dispensed into the insert. 0.5 ml/well of warm RPMI 1640 (10% FBS) at 36° C. was dispensed thereto. In the case of a positive control group, 0.5 ml of 36° C. RPMI 1640 (10% FBS) containing 2.5 ng/ml TGF-β was dispensed and used. Thereafter, the medium was exchanged every 3 days and the degree of invasion was observed, and on the 5th day, when the invasion of cancer cells was observed to have occurred sufficiently, the medium was removed, the cells were washed with 1×PBS, and then the cells inside the insert were scraped off with a cotton swab, and washed with 1×PBS to be removed so that no cells and matrigel residues were left inside the insert. 500 μl of 4% paraformaldehyde was dispensed into 24 wells with the outer side of the insert, incubated at room temperature for 5 minutes, washed three times with 1×PBS, and stained with a 0.05% crystal-violet solution for 5 minutes. After 5 minutes, the cells were washed 5 times with 1×PBS, and the degree of staining was dissolved in DMSO, and the wavelength was measured at 590 nm. When the absorbance of the control group was 1, the relative absorbance in each experimental group was calculated and graphed.

As a result of the study, in the experimental group expressing the vimentin phosphorylated point mutant protein, the absorbance value increased 4 to 6 times compared to the control group, similar to or higher than the positive control group, TGF-β treated group, the relative absorbance of the experimental group of the vimentin non-phosphorylated point mutant was relatively lower than the control group (FIG. 3F). Therefore, it was found that the vimentin non-phosphorylated point mutant was excellent in inhibiting the migration and invasion of lung cancer cells.

<Example 7> Evaluation of Metastasis and Tumorigenicity of Cancer Cells by Proteins Including Phosphorylation Sites of Vimentin and Non-Phosphorylated Point Mutations in Animal Model In order to observe the tumorigenicity of cancer cells in an animal model, the present inventors attempted to evaluate the effects of promoting and inhibiting tumorigenesis of cancer cells by using cancer cells in which phosphorylation and non-phosphorylation point genes of vimentin were expressed.

Specifically, NCI-H460 lung cancer cells ($2\times10^6$ cell count) stably expressing a vimentin protein containing point mutations were added in PBS and injected into the tail vein of mice, and the mice were raised for 8 weeks, and opened and then the metastasis and tumorigenicity of cancer cells were observed in the organs. For comparison, the metastasis and tumorigenesis of cancer cells were observed with respect to a control group (Mock; lentivirus-treated group in which a target gene was not expressed), a group administered with a vimentin protein-expressing NCI-H460 lung cancer cell line (WT), and groups administered with NCI-H460 lung cancer cell lines expressing phosphorylated point mutant vimentin proteins (S339E, T327E, and S83E) and groups administered with NCI-H460 lung cancer cell lines expressing non-phosphorylated point mutant vimentin proteins (S339A, T327A, and S83A). Experiments were performed on 5 mice for each experimental group, and the frequency of tumorigenesis, which was metastatic cancer in the lung, was measured and displayed in a graph (FIG. 4).

As illustrated in FIG. 4, most of the tumors were generated in the lungs, and accordingly, this experiment was also analyzed mainly in the lungs. Compared to the control group (Mock) and the vimentin wild type, tumorigenicity was relatively high in the experimental group injected with NCI-H460 cells expressing the vimentin protein including the phosphorylated point mutation. In particular, among the vimentin phosphorylated point mutants, the S339E experimental group showed the highest tumorigenicity when observing the number and size of tumors generated. Conversely, in the experimental group administered with NCI-H460 cells expressing the vimentin protein containing non-phosphorylation point mutations, relatively low tumorigenicity was observed (FIGS. 4A and 4B). In addition, as a result of observing the survival rate of each animal experimental group, it was confirmed that the survival rate of animals in the phosphorylated mutant experimental groups (S339E and S83E) was lower than that of the vimentin non-phosphorylated point mutant experimental group (FIG. 4C). In addition, through Haematoxylin and eosin (H&E) and Ki67 staining, it was found that the degree of cancer cell proliferation was high in the vimentin phosphorylated point mutant experimental group (FIGS. 4D to 4F). In animal models, it was confirmed that cancer cells expressing the phosphorylated point mutant of vimentin promoted cancer metastasis and tumorigenicity, whereas the non-phosphorylated point mutant inhibited the cancer metastasis and tumorigenicity.

Figure 4A:
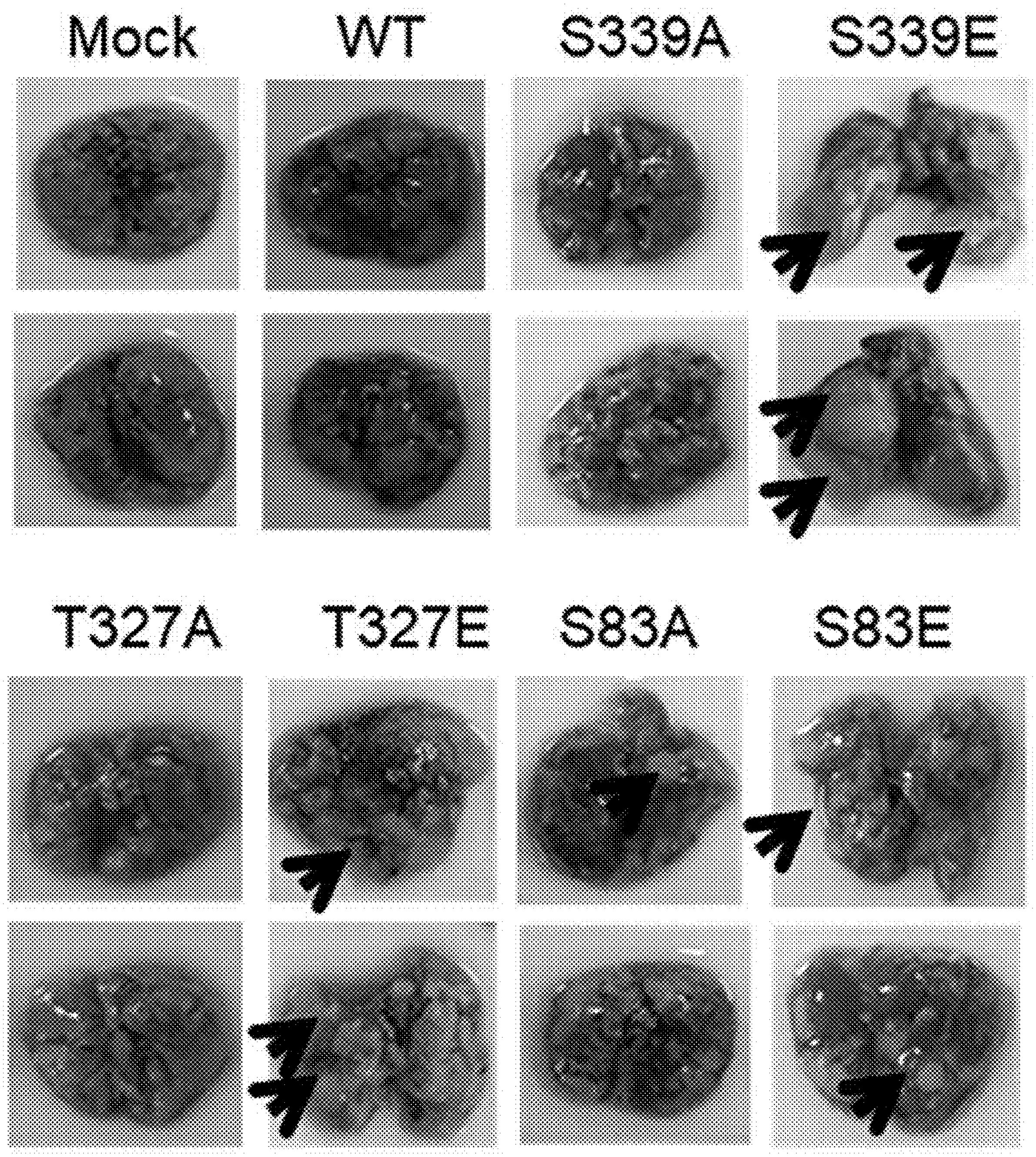
FIGS. 4A to 4H are experiments of measuring metastasis and tumorigenicity of cancer cells overexpressing phosphorylated and non-phosphorylated point mutants of vimentin in an animal model.
Figure 4B:
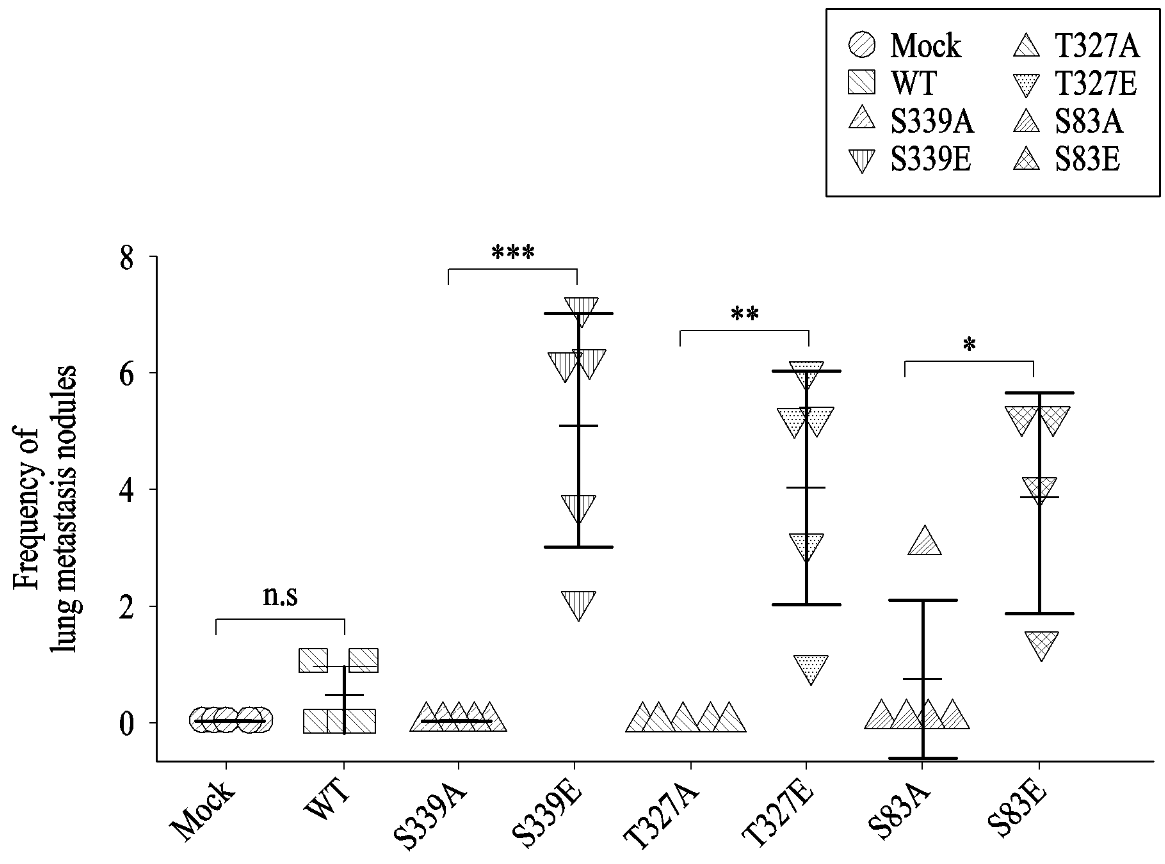
Figure 4C:
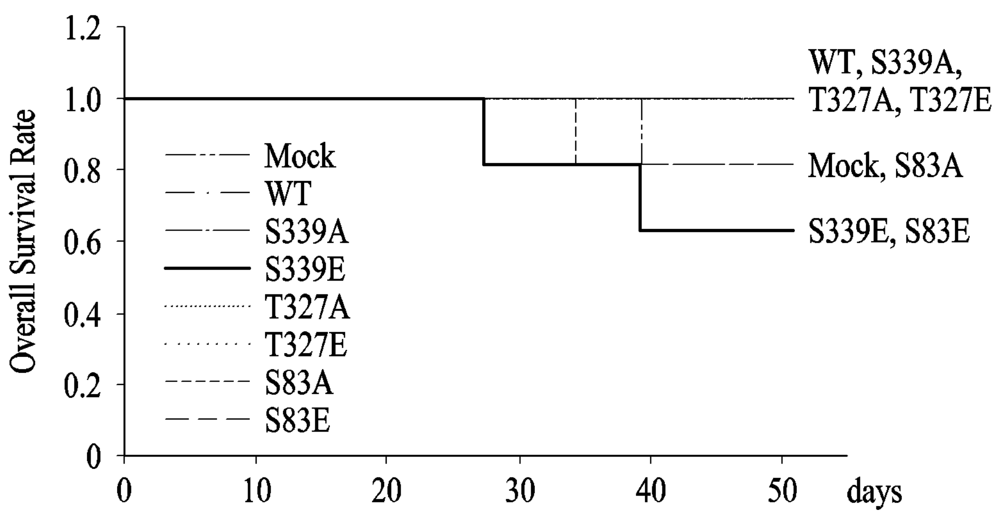
Figure 4D:
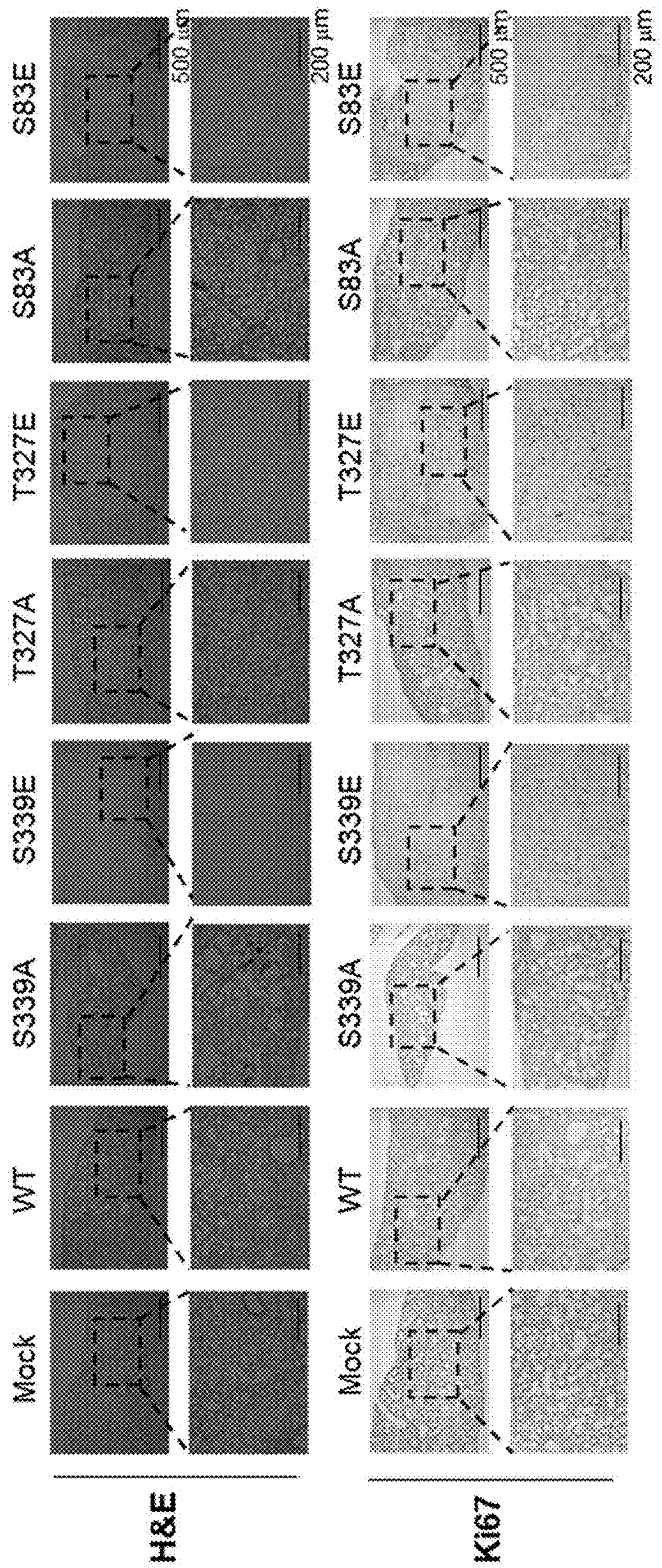
Figure 4E:
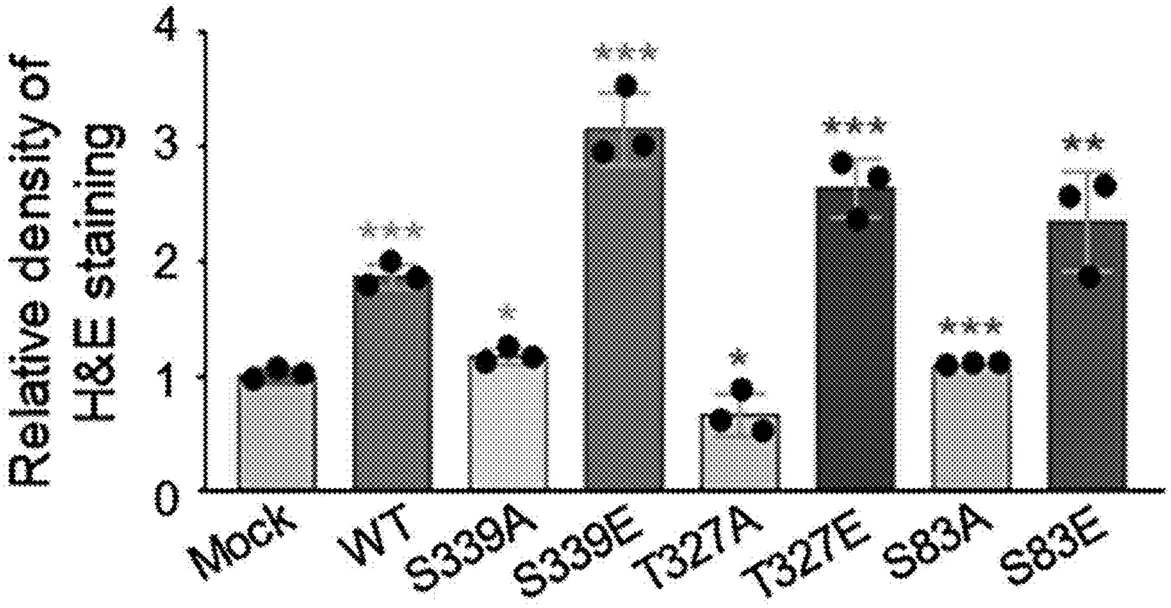
Figure 4F:
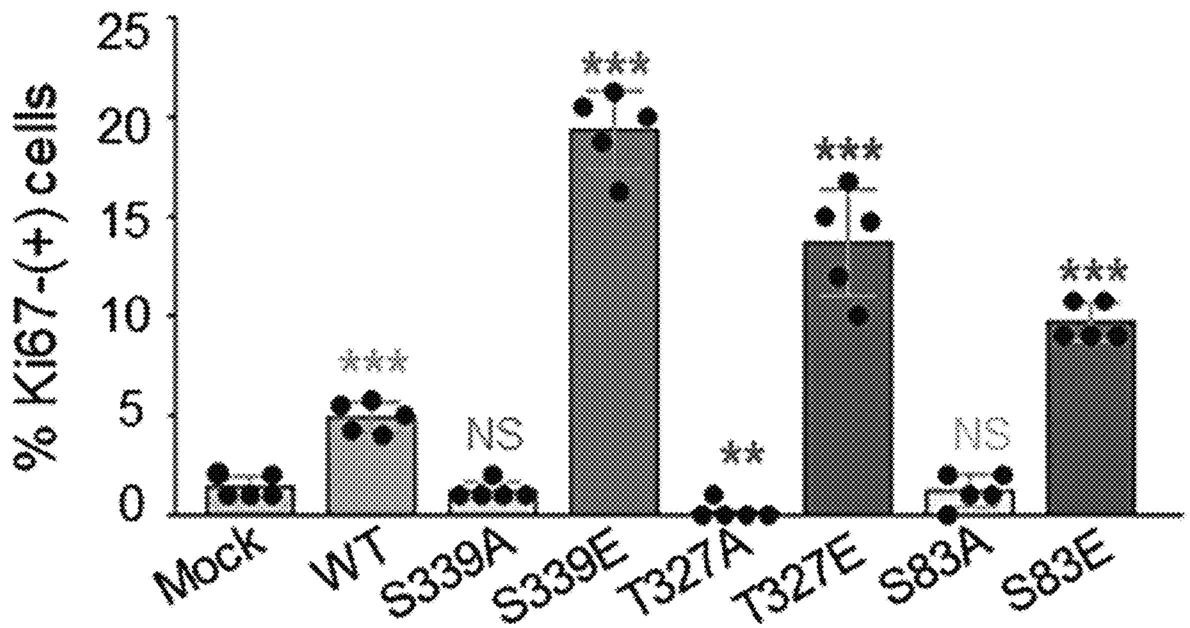
Figure 4G:
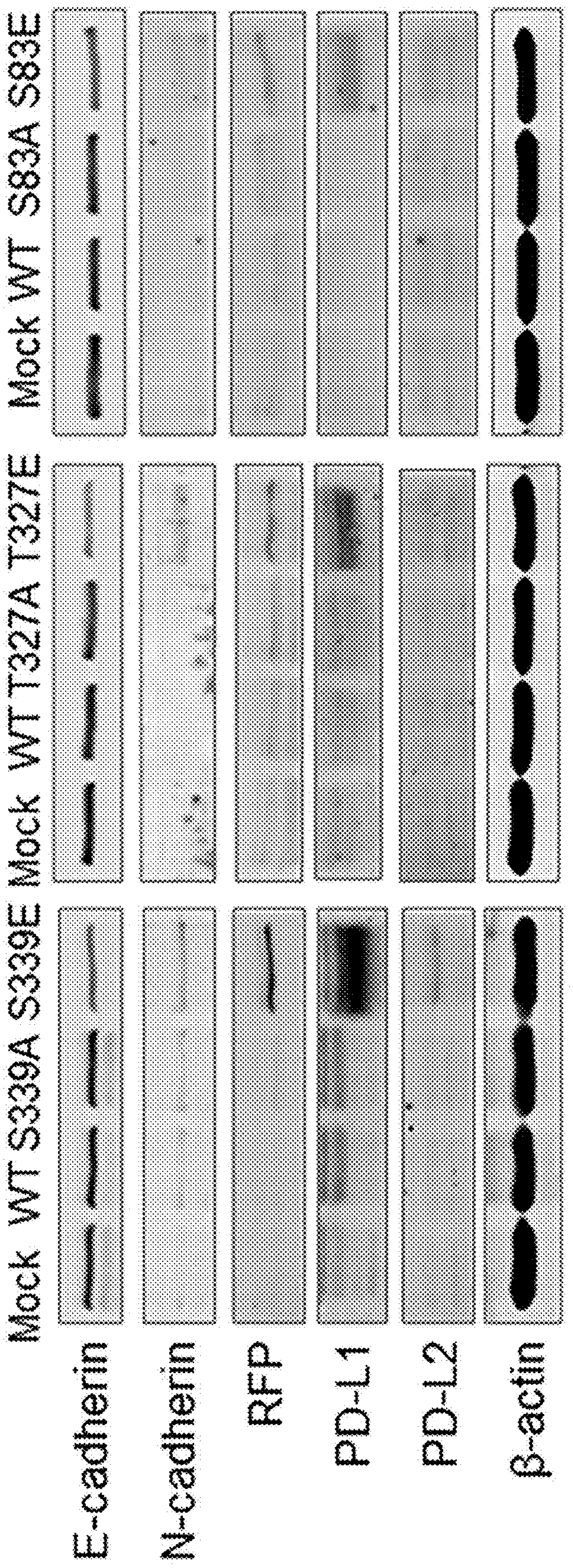
Figure 4H:
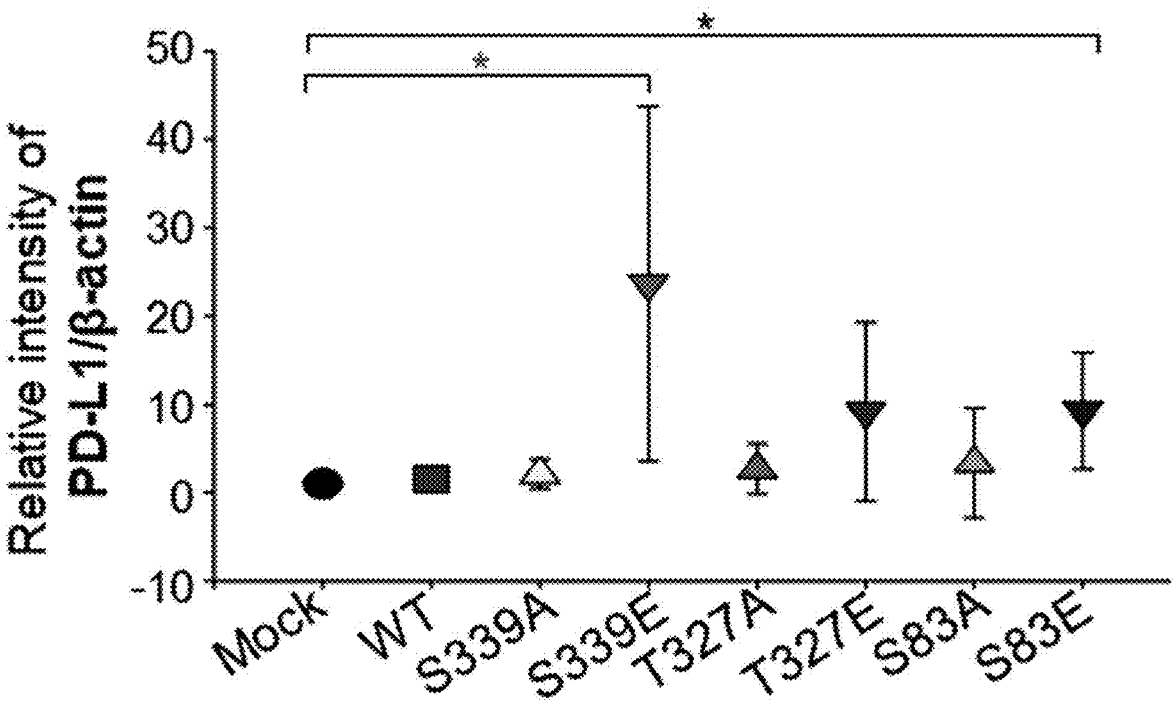

Next, as a result of lysing a part of the lung and observing the protein level of the epithelial-mesenchymal transition marker, in the experimental group of the vimentin phosphorylated point mutants, the protein level of N-cadherin, a mesenchymal marker, was increased, and the level of E-cadherin was decreased. In addition, as a result of confirming the expression of PD-L1 and PD-L2, known to increase the tumorigenicity of cancer cells by being involved in immune evasion, in each experimental group, the expression of PD-L1 was especially high in the vimentin phosphorylated point mutant experimental group (FIG. 4G). Among the vimentin phosphorylated point mutants which have been observed with the highest tumorigenicity, the expression of the PD-L1 protein was also the highest in the S339E experimental group (FIG. 4H). Therefore, it suggests that the phosphorylation of vimentin enhances epithelial-mesenchymal transition, metastasis, and tumorigenicity. On the other hand, it may be seen that the non-phosphorylated point mutants of the present disclosure, in particular, the S339A experimental group, have lower metastasis and a greater effect of inhibiting the tumorigenicity of cancer cells than the wild-type vimentin experimental group.

<Example 8> Evaluation of Inhibitory Effect of Vimentin shRNA on Epithelial-Mesenchymal Transition in Metastasis Environment by TGF-β Treatment In order to confirm the mRNA expression inhibitory effect of vimentin, shRNA and lentivirus containing the shRNA were prepared.

Specifically, in order to suppress vimentin mRNA expression, primers in Table 1 below were prepared to prepare shRNAs targeting each of nucleotide sequences at positions 1447 to 1467 (target #1), 1290 to 1310 (target #2), and 1132 to 1152 (target #3) of a human vimentin mRNA (Human vimentin mRNA [NM_003380]) sequence.

TABLE 1

| Target #no | Primer | Sequence | SEQ ID No. |
|---|---|---|---|
| Target #1 | Forword | 5'-CCGGGTGAAATGGAAGAGAACTTTGCTCGAGCAAAGTTCTCTTCCATTTCACTTTTTG-3' | 5 |
| | Reverse | 5'-AATTCAAAAAGTGAAATGGAAGAGAACTTTGCTCGAGCAAAGTTCTCTTCCATTTCAC-3 | 6 |
| Target #2 | Forword | 5'-CCGGGCAGAAGAATGGTACAAATCCCTCGAGTTATTTGTACCATTCTTCTGCTTTTTG-3 | 7 |
| | Reverse | 5'-AATTCAAAAAGCAGAAGAATGGTACAAATCCCTCGAGTTATTTGTACCATTCTTCTGC-3 | 8 |
| Target #3 | Forword | 5'-CCGGTGAAGAAACTCCACGAAGAGGCTCGAGCCTCTTCGTGGAGTTTCTTCATTTTTG-3' | 9 |
| | Reverse | 5'-AATTCAAAAATGAAGAAACTCCACGAAGAGGCTCGAGCCTCTTCGTGGAGTTTCTTCA-3' | 10 |

The prepared shRNAs were shown in Table 2 below.

TABLE 2

| shRNA #no | Sequence | SEQ ID No. |
|---|---|---|
| shRNA #1 | GTGAAATGGAAGAGAACTTTG | 11 |
| shRNA #2 | GCAGAAGAATGGTACAAATCC | 12 |
| shRNA #3 | TGAAGAAACTCCACGAAGAGG | 13 |

Based on this, a pLKO-puro.1-vimentin shRNA plasmid was constructed using a pLKO-puro.1 vector. The plasmid was expressed through HEK293 cell transfection together with pHR'-CMV-VSVG and pHR'-CMV-deltaR8.2, and the culture medium of the cells was collected to produce lentivirus. The lentivirus was concentrated using a centrifuge. To confirm the virus expression, NCI-H460 and A549 cells were cultured at $5\times10^4$ cells/ml, and then on the next day, lentivirus was added to 20 μ/well in an infection buffer (10 mM HEPES, 1 mg/ml polybrene) to infect cancer cells. After 24 hours, vimentin shRNA-infected cells were selected by treating puromycine for 48 hours. First, the present inventors confirmed the mRNA expression and protein expression levels of vimentin in cells infected with each vimentin shRNA selected through puromycine treatment in order to confirm the effect of suppressing the vimentin expression by the prepared vimentin shRNA.

Figure 5A:
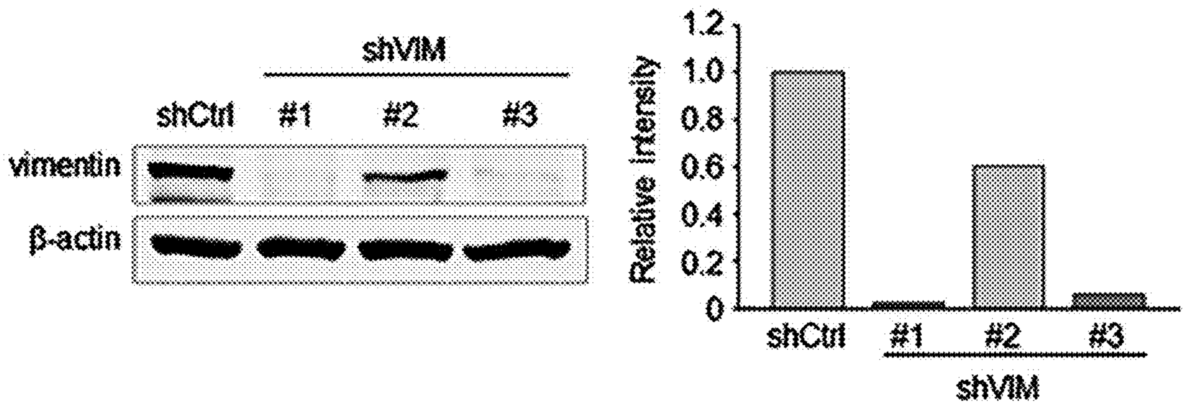
FIGS. 5A and 5B are results of observing an effect of inhibiting the vimentin expression when treated with each vimentin shRNA prepared to suppress vimentin mRNA expression in lung cancer cells.
Figure 5B:
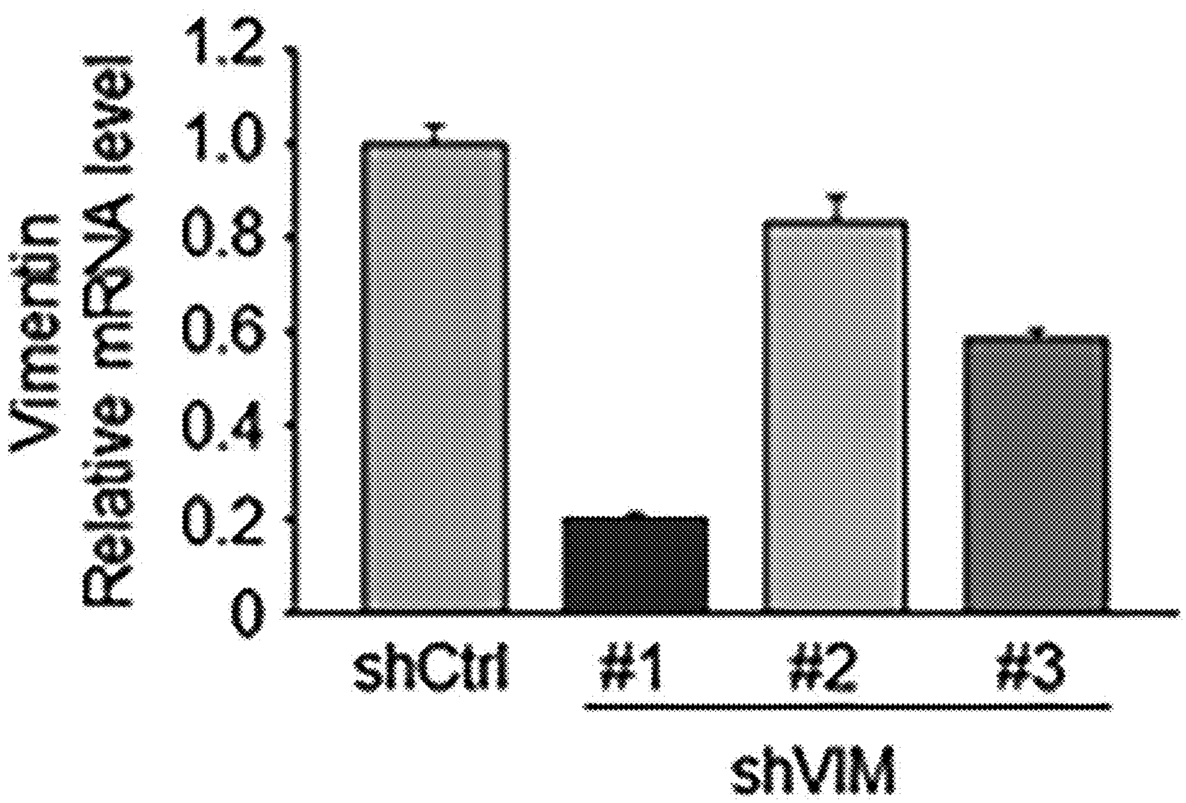

As illustrated in FIG. 5, it was observed that the expression of vimentin mRNA was reduced in lung cancer cells NCI-H460 infected with each vimentin shRNA (shvimentin) compared to cells infected with control shRNA (shCtrl), and the vimentin expression was suppressed. In particular, shRNA targeting the nucleotide sequence at positions 1447 to 1467 (target #1) in the vimentin mRNA sequence was observed to have the best effect of suppressing the vimentin expression. Accordingly, the present inventors used shRNA targeting the nucleotide sequence at positions 1447 to 1467 (target #1) in the vimentin mRNA sequence in the study of suppressing the vimentin expression below.

The present inventors observed changes in mRNA expression and protein expression of epithelial-mesenchymal transition markers and related factors, when cancer metastasis induced by treatment with TGF-β suppressed vimentin mRNA expression by vimentin shRNA treatment.

The constructed vimentin-inhibiting cell line was treated with 2.5 ng/ml TGF-β for 48 hours to observe the expression of CDH1 and CDH2 as epithelial-mesenchymal transition-related factors and the expression of PD-L1 as an immune evasion-related factor through real-time PCR and immunoblot analysis under conditions for inducing cancer metastasis (FIGS. 6A to 6D).

As illustrated in FIG. 6, it was observed that the expression of vimentin mRNA was reduced in lung cancer cells NCI-H460 and A549 infected with each vimentin shRNA (shvimentin) compared to cells infected with control shRNA (shCtrl), and the vimentin expression was suppressed even under the conditions treated with TGF-β, which induced a cancer metastasis environment (FIGS. 6A and 6C). In addition, it was observed that the decrease in the expression of CDH1 as an epithelial marker by TGF-β treatment was suppressed by the inhibition of the expression of vimentin by shvimentin treatment, and the increase in the expression of PD-L1, including CDH2 as a mesenchymal marker by TGF-β treatment was also suppressed by the inhibition of the expression of vimentin (FIGS. 6B and 6D).

<Example 9> Evaluation of Metastatic Inhibitory Effect of Vimentin shRNA

The present inventors demonstrated that the expression inhibition of vimentin by vimentin shRNA treatment inhibited the cell migration through a migration assay in a TGF-β-treated metastasis environment.

Specifically, lung cancer cells NCI-H460 were infected with control shRNA (shCtrl) or vimentin shRNA (shvimentin) virus. On the next day, after treatment with 2 μg/ml puromycin for 48 hours, the cells expressing the selected vimentin shRNA were dispensed at $2\times10^5$ cells/ml in a 6-well plate, and after 24 hours, scratched at regular intervals using a pipette tip. In a migration experiment, cancer metastasis was induced using 2.5 ng/ml of TGF-β. After scratching, the intervals and migration of cells were observed under a microscope at 24-hour intervals, and the degree of restoration of the intervals was measured as distances between cells through cell imaging under the microscope. When the measured value was 100% as the distance of the control group, the relative migration distance was calculated, and a graph was displayed as % (FIG. 6E).

$$\text{Relative migration distance (\%)} = \text{measured value in experimental group} \times 100/\text{measured value in control group}$$

As a result of the study, the metastasis of lung cancer cells themselves was reduced by the suppression of vimentin expression by vimentin shRNA treatment, and particularly, when the migration of the control group was set to 0%, the migration was reduced by about-10% or more at 72 hours. At 72 hours, the migration was increased by about 30% compared to the control group by TGF-β treatment, and the metastasis of these lung cancer cells was reduced by about-8% by vimentin shRNA. Therefore, it was found that the suppression of vimentin expression by vimentin shRNA had a strong inhibitory effect on not only the metastasis of cancer cells themselves but also the metastasis induced by TGF-β treatment.

<Example 10> Evaluation of Invasion Inhibitory Effect of Vimentin shRNA

Next, the present inventors demonstrated that the expression inhibition of vimentin inhibited the cell invasion through an invasion assay in a TGF-β-treated metastasis environment.

For the present disclosure, the matrigel was completely dissolved at 4° C. for 16 to 20 hours, and then diluted with cold serum-free RPMI 1640 (4° C.) to become a concentration of 1 mg/ml. 100 μl of a matrigel mixture was added into an 8.0 μm, 24 well insert and solidified in a 37° C. incubator for 12 to 20 hours. Lung cancer cell NCI-H460, in which the vimentin expression was suppressed by vimentin shRNA treatment, was diluted in a serum-free medium at a cell count of $1\times10^5$ cells/well and dispensed on the solidified matrigel. 0.5 ml/well of warm RPMI 1640 (10% FBS) at 36° C. containing serum was dispensed thereto. Cancer metastasis was induced by TGF-β treatment. Thereafter, the medium was exchanged every 3 days and the degree of invasion was observed, and on the 5th day, when the invasion of cancer cells was observed to have occurred sufficiently, the medium was removed, the cells were washed with 1×PBS, and then the cells inside the insert were scraped off with a cotton swab, and washed with 1×PBS to be removed so that no cells and matrigel residues were left inside the insert. Cells that 500 μl of 4% paraformaldehyde was dispensed into a 24 well plate with the outer side of the insert and invaded with matrigel, were incubated at room temperature for 5 minutes, washed three times with 1×PBS for 5 minutes, and stained with a 0.05% crystal-violet solution for 5 minutes. The stained cells were observed under a microscope and the number thereof was counted, and the number of invaded cells was graphed.

As a result, as illustrated in FIG. 6F, it was observed that cells infected with vimentin shRNA to suppress the expression of vimentin inhibited the cell invasion more than cells treated with the control virus (shCtrl), and the suppression of the vimentin expression by vimentin inhibited the cell invasion even in the metastasis environment by TGF-β treatment.

As the results together, it was demonstrated that the suppression of the vimentin expression by vimentin shRNA not only inhibited the expression of factors involved in epithelial-mesenchymal transition of cells, but also reduced the cell migration and invasion, and even in the metastasis environment by TGF-β treatment, the suppression of the vimentin expression by vimentin shRNA inhibited the expression of factors related to epithelial-mesenchymal transition, and also reduced the migration and invasion of cells.

<Example 11> Evaluation of Tumorigenicity Inhibitory Effect of Vimentin shRNA

The present inventors conducted a colony formation assay (soft agar assay) using soft agar to confirm an effect of inhibiting the tumorigenicity of cancer cells by suppressing the expression of vimentin in a metastatic environment treated with TGF-β. Specifically, in order to make a 0.6% agar layer at the bottom, 150 ml of 4% stock agar, 100 ml of FBS, and 750 ml of Free RPMI 1640 were mixed, and a total of 1 ml of the agar medium was added into a 12 well diameter plate and solidified for 1 hour. To make a 0.4% agar layer on the top, 100 ml of 4% stock agar and 100 ml of FBS were mixed with 800 ml of an RPMI1640 medium containing $1\times10^3$ cells, solidified for 1 hour, and then dispensed with 10% FBS. The medium was changed every 5 days, and after 2 weeks, it was observed that colonies, which are tumor masses, were formed under a microscope, and the colonies were stained with a 0.005% crystal violet-methanol solution for 15 minutes, and then washed with a 20% methanol-PBS solution, and the total number of colonies was measured under a microscope.

As a result of the study, it was observed that in the case of a positive control group treated with 2.5 ng/ml TGF-β, colony formation increased by about 2 times compared to the control group, and in the cells of a vimentin expression suppression group, the number of colonies was reduced compared to the control group. In addition, it was confirmed that the inhibition of vimentin expression reduced the number of colonies in the environment of cancer metastasis induced by TGF-β treatment. Accordingly, it was found that the suppression of the vimentin expression by vimentin shRNA was an important factor in suppressing tumorigenesis (colony formation) of cancer cells (FIG. 6G).

<Example 12> Evaluation of Metastasis and Invasion Promoting Effects by Expression of Vimentin Phosphorylated Point Mutant Protein after Suppression of Expression by Vimentin shRNA Through previous experiments, the present inventors confirmed that the suppression of vimentin expression by vimentin shRNA inhibited cancer metastasis and tumorigenicity. Under these conditions, the effect of the re-expression of the protein of vimentin phosphorylated point mutant on cancer metastasis and invasion was analyzed.

Figure 6H:
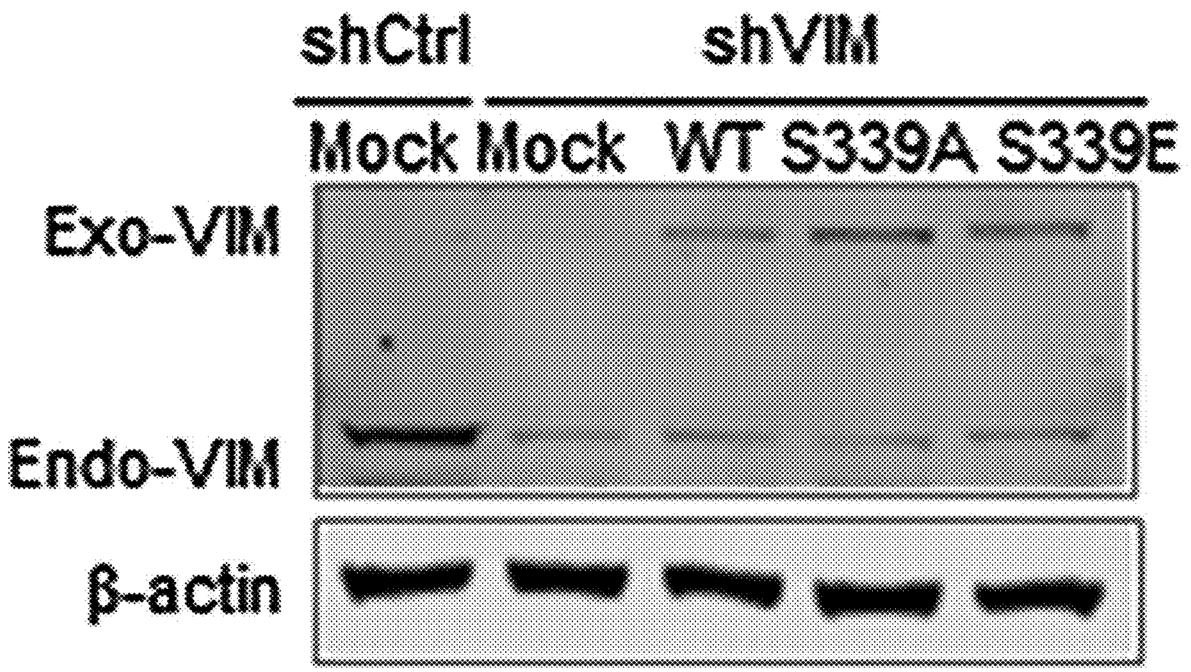

Specifically, 20 μl of viral vimentin shRNA expressed using pLKO-puro.1-vimentin prepared to suppress the expression of vimentin mRNA in lung cancer cells NCI-H460 was taken and mixed with an infection buffer (10 mM HEPES, 1 μg/ml Polybrene) and treated in the cells. After 24 hours, 2 μg/ml puromycin was treated for 48 hours, and only the cells infected with vimentin shRNA were selected to construct a cell line that suppressed the vimentin expression. The constructed vimentin expression-suppressing cell line was infected with lentiviruses expressing a wild type and phosphorylated point mutant (S339E) and non-phosphorylated point mutant (S339A) of vimentin, and then selected with puromycin and G418. After selecting, the cell line was treated with 1 μg/ml doxycycline to induce the expression of the wild type and the phosphorylated and non-phosphorylated point mutants of vimentin again, and then the protein expression level was confirmed to confirm whether each point mutant of vimentin was expressed well. As illustrated in FIG. 6H, it was confirmed that the wild type and each point mutant of vimentin were well expressed under the condition in which the vimentin expression was suppressed.

Next, the present inventors demonstrated the effect of re-expression of the protein of the phosphorylated point mutant of vimentin on the migration and invasion of cancer cells under the condition of suppressing the vimentin expression.

First, in order to see the effect on the migration of cancer cells, specifically, NCI-H460 cells re-expressing the wild type (WT) and the phosphorylated (S339E) and non-phosphorylated (S339A) point mutants of vimentin constructed in the previous experiment were diluted in a serum-free medium, $5\times10^4$ cells were dispensed into a 8.0 μm, 24-well insert, and a medium containing 10% serum was dispensed into a 24-well plate, and then added with the insert. After 48 hours of cell dispensation, the migrated cells were immobilized by dispensing 500 μl of 4% paraformaldehyde, washed three times with 1×PBS, and then stained with a 0.05% crystal-violet solution for 5 minutes. After 5 minutes, the cells washed 5 times with 1×PBS, and the staining intensity was measured using an Odyssey infrared imaging system. When the staining intensity of the control group was 1, a relative staining intensity in each experimental group was calculated and a graph was displayed.

Figure 6I:
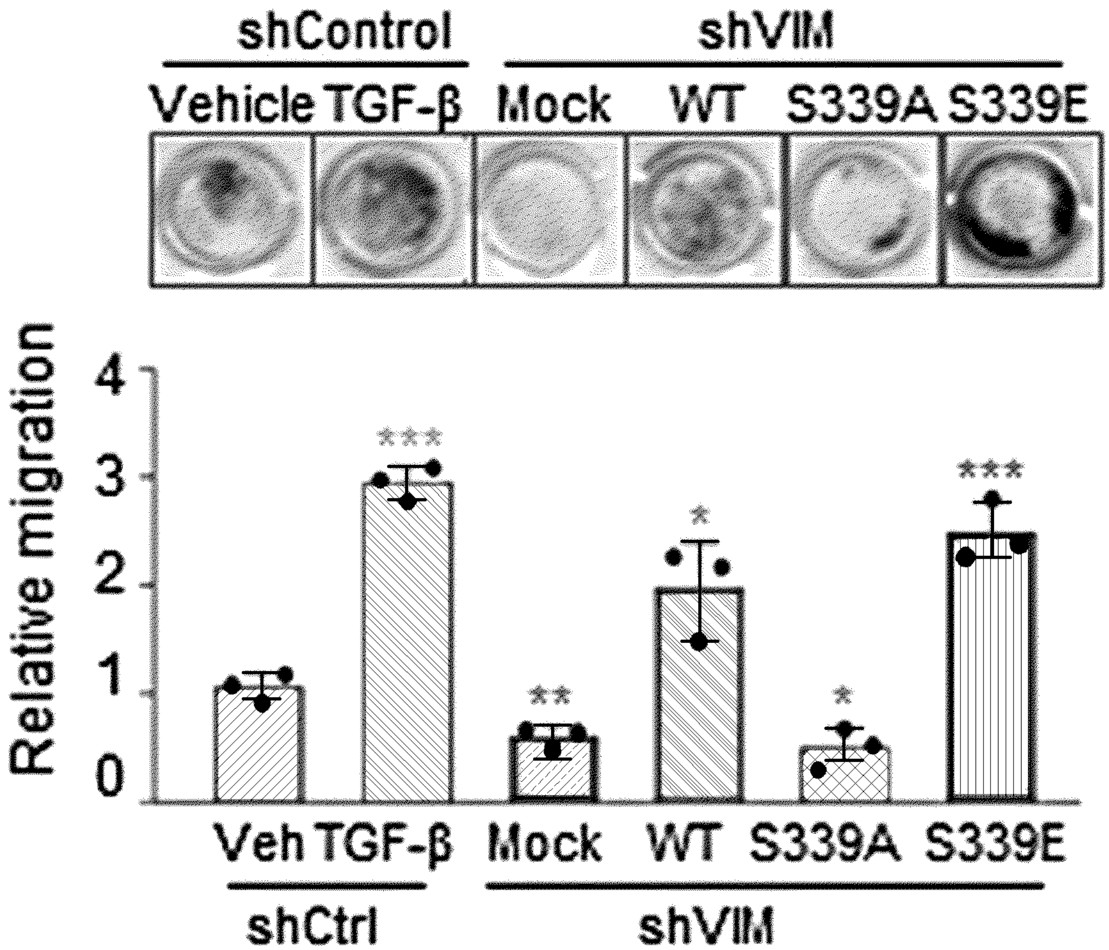

As a result, as illustrated in FIG. 6I, in cells in which the vimentin expression was suppressed, cells in which the vimentin wild type (WT) was expressed again showed increased cell migration as compared to control cells (Mock), and in cells expressing S339E, a phosphorylated point mutant of vimentin, the cell migration was increased as compared with a positive control group treated with TGF-β. Accordingly, it was found that the phosphorylation of vimentin had a strong promoting effect on cancer cell metastasis.

Next, the present inventors demonstrated the effect of re-expression of the protein of the phosphorylated point mutant of vimentin on the invasion under the condition of suppressing the vimentin expression.

For the present disclosure, NCI-H460 cells re-expressing vimentin wild type (WT) and phosphorylated (S339E) and non-phosphorylated (S339A) point mutants constructed in the previous experiment were diluted with a serum-free medium at a cell count of $1\times10^5$ cells/well and dispensed on the solidified matrigel. 0.5 ml/well of warm RPMI 1640 (10% FBS) at 36° C. containing serum was dispensed thereto. After 5 days of cell dispensation, the medium was removed and the cells were washed with 1×PBS, and then the cells inside the insert were scraped off with a cotton swab and washed with 1×PBS to remove the cells and the matrigel residues so as not to be left inside the insert. Cells that 500 μl of 4% paraformaldehyde was dispensed into a 24-well plate with the outer side of the insert and invaded with matrigel, were incubated at room temperature for 5 minutes, washed three times with 1×PBS for 5 minutes, and stained with a 0.05% crystal-violet solution for 5 minutes. After 5 minutes, the cells were washed 5 times with 1×PBS, and the degree of staining was measured at the wavelength of 590 nm. When the absorbance of the control group was 1, the relative absorbance in each experimental group was calculated and graphed.

Figure 6J:
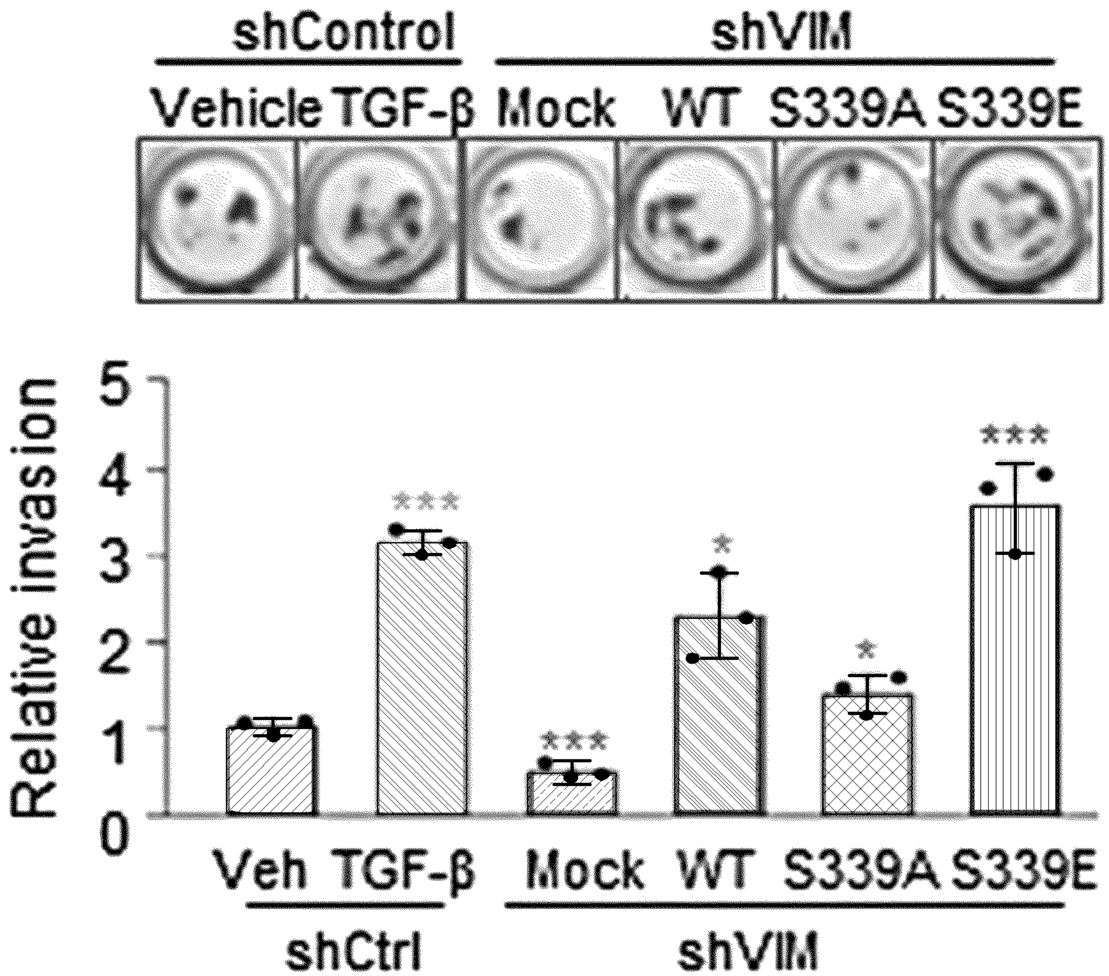

As a result, as illustrated in FIG. 6J, cells infected with vimentin shRNA to suppress the vimentin expression inhibited the cell invasion compared to cells treated with control virus (shCtrl), the vimentin wild type (WT)-expressed cells under these conditions showed increased cell invasion compared to the control cells (Mock), and cells expressing S339E, a phosphorylation point mutation of vimentin, exhibited a greater increase in cell invasion than the TGF-β-treated positive control. Accordingly, it was found that the phosphorylation of vimentin had a strong promoting effect on the invasion of cancer cells.

As the results together, it was demonstrated that the phosphorylation of vimentin increases the migration and invasion of cells even under the condition of suppressing the vimentin expression by vimentin shRNA.

As described above, specific parts of the present disclosure have been described in detail, and it will be apparent to those skilled in the art that these specific techniques are merely preferred embodiments, and the scope of the present disclosure is not limited thereto. Therefore, the substantial scope of the present disclosure will be defined by the appended claims and their equivalents.

INDUSTRIAL APPLICABILITY

The vimentin mutants and/or shRNA of the present disclosure are treated separately or in combination to act only on cancer cells, especially metastatic cancer, without affecting normal cells and may be usefully used for the treatment of primary and metastatic solid cancers, leukemia, and the like caused by abnormal cell growth.

The invention claimed is:

1. A vimentin mutant protein comprising an amino acid sequence of SEQ ID NO: 1 or SEQ ID NO: 2.

2. The vimentin mutant protein of claim 1, wherein the protein comprises the amino acid sequence of SEQ ID NO: 1, and amino acid at position 327 of SEQ ID NO: 1 is alanine.

3. The vimentin mutant protein of claim 1, wherein the protein comprises the amino acid sequence of SEQ ID NO: 2, and amino acid at position 339 of SEQ ID NO: 2 is alanine.

4. A recombinant vector comprising a gene encoding the protein of claim 1.

5. The recombinant vector of claim 4, wherein the gene is SEQ ID NO: 3 or SEQ ID NO: 4.

6. The recombinant vector of claim 4, wherein the vector is a lentiviral vector.

7. A pharmaceutical composition for the treatment of cancer, comprising the vimentin mutant protein of claim 1 or the vector of claim 4 as an active ingredient.

8. The pharmaceutical composition for the treatment of cancer of claim 7, wherein the composition inhibits cancer metastasis by reducing the migration and invasion of cancer cells.

9. A method for treating non-small cell lung cancer in a subject in need thereof, comprising administering to the subject an effective amount of a vimentin mutant protein comprising an amino acid sequence of SEQ ID NO: 1 or SEQ ID NO: 2, or a recombinant vector comprising a gene encoding the vimentin mutant protein.

10. The method of claim 9, wherein the non-small cell lung cancer is adenocarcinoma.

11. A pharmaceutical composition for treatment of cancer comprising shRNA for inhibiting the expression of a vimentin protein or a vector expressing the shRNA, wherein the shRNA comprises a nucleotide sequence, wherein the nucleotide sequence comprises SEQ ID NO: 11.

12. The pharmaceutical composition of claim 11, wherein the composition inhibits cancer metastasis by reducing the migration and invasion of cancer cells.

13. The pharmaceutical composition of claim 11, wherein the composition inhibits tumorigenicity.

14. The pharmaceutical composition of claim 11, further comprising:

a vimentin mutant comprising an amino acid sequence of SEQ ID NO: 1 or SEQ ID NO: 2.

15. The pharmaceutical composition of claim 11, further comprising:

a vector loaded with a gene consisting of a nucleotide sequence of SEQ ID NO: 3 or SEQ ID NO: 4.

16. A method for treating a non-small cell lung cancer in a subject in need thereof, comprising administering to the subject an effective amount of shRNA for inhibiting the expression of a vimentin protein or a vector expressing the shRNA, wherein the shRNA comprises a nucleotide sequence of SEQ ID NO: 11.

17. The method of claim 16, wherein the non-small cell lung cancer is adenocarcinoma.

* * * * *